(12) United States Patent
John

(10) Patent No.: US 11,980,602 B2
(45) Date of Patent: May 14, 2024

(54) CANNABINOID PRODRUG COMPOUNDS

(71) Applicant: Firstlight Pharmaceuticals LLC, Pennington, NJ (US)

(72) Inventor: Kieran John, Pennington, NJ (US)

(73) Assignee: Firstlight Pharmaceuticals LLC, Pennington, NJ (US)

( * ) Notice: Subject to any disclaimer, the term of this patent is extended or adjusted under 35 U.S.C. 154(b) by 0 days.

(21) Appl. No.: 17/703,068

(22) Filed: Mar. 24, 2022

(65) Prior Publication Data

US 2022/0211656 A1 Jul. 7, 2022

Related U.S. Application Data

(63) Continuation of application No. PCT/US2020/052829, filed on Sep. 25, 2020.

(60) Provisional application No. 62/906,228, filed on Sep. 26, 2019.

(51) Int. Cl.
| | | |
|---|---|---|
| *A61K 31/27* | (2006.01) | |
| *A61K 45/06* | (2006.01) | |
| *C07C 271/54* | (2006.01) | |

(52) U.S. Cl.
CPC .............. *A61K 31/27* (2013.01); *A61K 45/06* (2013.01); *C07C 271/54* (2013.01)

(58) Field of Classification Search
CPC ........ C07C 271/54; A61K 31/27; A61P 35/00
See application file for complete search history.

(56) References Cited

U.S. PATENT DOCUMENTS

| | | |
|---|---|---|
| 2009/0036523 A1 | 2/2009 | Stinchcomb et al. |
| 2017/0298399 A1 | 10/2017 | Peet et al. |
| 2020/0388642 A1 | 12/2020 | Fu et al. |

FOREIGN PATENT DOCUMENTS

| | | | |
|---|---|---|---|
| JP | 2022535238 A | | 8/2022 |
| WO | WO2008107879 | * | 9/2008 |
| WO | 2009018389 A1 | | 2/2009 |
| WO | 2017132526 A1 | | 8/2017 |
| WO | 2018091551 A1 | | 5/2018 |

OTHER PUBLICATIONS

International Search Report and Written Opinion for International Application No. PCT/US20/52829, filed Sep. 25, 2020, dated Mar. 12, 2021.
Ferro, R., et al., GPR55 signalling promote proliferation of pancreatic cancer cells and tumour growth in mice, and its inhibition increases effects of gemcitabine, Oncogene, vol. 37, p. 6368-6382 (2018).
PubChem CID 129280 Create Date: Aug. 8, 2005.
Donadelli et al: "Gemcitabine/cannabinoid combination triggers autophagy in pancreatic cancer cells through a ROS-mediated mechanism", Cell Death and Disease, vol. 2, No. 4, Apr. 1, 2011 (Apr. 1, 2011), pp. e152-e152.

\* cited by examiner

*Primary Examiner* — Barbara P Badio
(74) *Attorney, Agent, or Firm* — Fox Rothschild LLP

(57) ABSTRACT

A prodrug compound of cannabidiol (CBD), pharmaceutical composition thereof and methods of use thereof in patients in need.

27 Claims, 10 Drawing Sheets

COMPOUND A

CANNABINOID PRODRUG COMPOUNDS

CROSS-REFERENCE TO RELATED APPLICATIONS

The present application is a bypass continuation of International Application No. PCT/US20/52829, filed Sep. 25, 2020, which claims priority to U.S. Provisional Application No. 62/906,228, filed Sep. 26, 2019, which is incorporated herein by reference in its entirety.

FIELD OF INVENTION

The present disclosure relates to cannabinoid prodrug compounds and method of using such compounds in patients in need thereof.

BACKGROUND

Current scientific evidence suggests that cannabinoids plays a role in maintaining the homeostasis among the immune system & central and peripheral nervous systems. Positive and negative feedback loops caused by the effects of cannabinoids alter different physiological processes. A variety of diseases can result when normal equilibrium is not achieved including those that involve neurologic, endocrine and oncolytic functions.

Cannabinoids are compounds derived from *Cannabis sativa*, an annual plant in the Cannabaceae family. The plant contains about 60 cannabinoids. The most active naturally occurring cannabinoid is tetrahydrocannabinol (THC), which is used for the treatment of a wide range of medical conditions, including glaucoma, AIDS wasting, neuropathic pain, treatment of spasticity associated with multiple sclerosis, fibromyalgia and chemotherapy-induced nausea. Additionally, THC is particularly effective as an anti-emetic drug and is administered to curb emesis, a common side effect accompanying the use of opioid analgesics and anesthetics, highly active anti-retroviral therapy and cancer chemotherapy.

Other cannabinoid or intermediate components that may be present in herbal cannabis include but may not be limited to Cannabidiolic acid (CBDA), Cannabigerolic acid (CBGA), Cannabinol (CBN), Cannabichromenic acid (CBCA), Cannabichromene (CBC), Cannabinolic acid (CBNA), and Cannabidiol (CBD). Cannabidiol was formerly regarded as an inactive constituent, however there is emerging evidence that it has pharmacological activity, which is different from that of THC in several respects. Further, the medical use of cannabinoids has been historically hindered not only by the deficiencies in standardized methods of manufacturing, identifying and validating the reproducibility methodologies, stability and other difficult physicochemical properties that limit the bioavailability and efficiency of these compounds for specific site delivery; but also because of an inability to target precisely and specifically the biochemistry and physiology in the body. The present invention addresses this shortcoming in the art.

SUMMARY OF THE INVENTION

This patent document discloses cannabinoid prodrug compounds that provide site specific delivery to an area of interest. At least one embodiment is directed to prodrugs of cannabidiol (CBD). The present prodrug compounds overcome deficiencies in the physicochemical properties of CBD that limit formulation options while enhancing delivery of CBD to a target site of interest. In addition, key pharmaceutical properties including solubility, permeability or partitioning, chemical or enzymatic stability and transporter affinities can be improved.

An aspect of the disclosure provides a prodrug compound represented by Formula I, Formula I

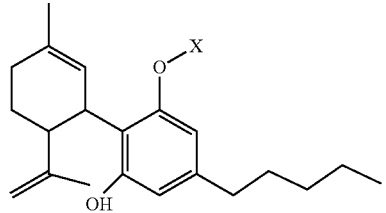

wherein:
X is

Formula X-a

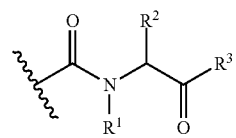

wherein:
$R^1$ is selected from the group consisting of H, $C_{1-10}$ alkyl, $C_{1-4}$ alkyl-aryl, $C_{1-4}$ alkyl- and heteroaryl;

$R^2$ is H, or $C_{1-10}$ alkyl optionally substituted with OH, SH, $SC_{1-4}$ alkyl, heteroaryl (e.g. indolyl), CONH2, COOH, NH2, NHC(NH)NH2, imidazolyl, or aryl (e.g. phenyl) optionally substituted with $C_{1-4}$ alkyl or OH;

and $R^3$ is selected from the group consisting of $C_{1-10}$ alkyl, $C_{1-4}$ alkyl-aryl, $C_{1-4}$ alkyl-heteroaryl, and Formula Y

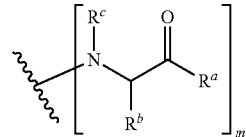

wherein
$R^a$ in each instance is independently OH, $NHC_{1-10}$alkyl or $OC_{1-10}$alkyl, provided that $R^a$ is a covalent bond when $R^a$ is in a non-terminal position;

$R^b$ in each instance is independently H, or $C_{1-10}$ alkyl optionally substituted with OH, SH, $SC_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and m is an integer ranging from 1 to 9;

Formula X-b

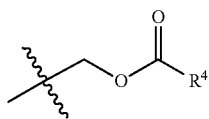

b)

wherein:

$R^4$ is selected from the group consisting of H, $C_{1-10}$ alkyl, $C_{1-4}$ alkyl-aryl, $C_{1-4}$ alkyl-heteroaryl and Formula Z

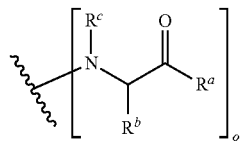

wherein $R^a$ in each instance is independently OH, $NHC_{1-10}$alkyl or $OC_{1-10}$ alkyl, provided that $R^a$ is a covalent bond when $R^a$ is in a non-terminal position; and m is 1 to 9;

$R^b$ in each instance is independently H or $C_{1-10}$ alkyl optionally substituted with OH, SH, $SC_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and o is an integer ranging from 1 to 9;

c) $(A)_n$ (Formula X-c), wherein A is an amino acid residue, wherein each A is independently represented by

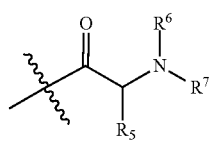

wherein:

$R^5$ is H or $C_{1-10}$ alkyl optionally substituted with OH, SH, $SC_{1-4}$ alkyl, heteroaryl (e.g. indolyl), CONH2, COOH, NH2, NHC(NH)NH2, imidazolyl, or aryl (e.g. phenyl) optionally substituted with $C_{1-4}$ alkyl or OH;

$R^6$ and $R^7$ in each instance are each independently s H, or $C_{1-10}$ alkyl optionally substituted with OH, SH, $SC_{1-4}$ alkyl, heteroaryl, CONH2, COOH, NH2, or aryl; provided that $R^7$ is a covalent bond to a carbonyl group if the amino acid residue is in a non-terminal position;

Optionally $R^5$ and $R^6$ link up to form a 5 to 7 membered ring;

n is an integer from 1 to 9, inclusive;

Formula X-d

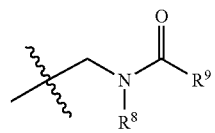

d)

wherein:

$R^8$ is selected from the group consisting of H, $C_{1-10}$ alkyl, $C_{1-4}$ alkyl-aryl, $C_{1-4}$ alkyl-heteroaryl; $R^9$ is selected from the group consisting of $C_{1-10}$ alkyl, $C_{1-4}$ alkyl-aryl, $C_{1-4}$ alkyl-heteroaryl, and Formula P

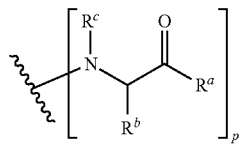

wherein $R^a$ in each instance is OH, $NHC_{1-10}$ alkyl or $OC_{1-10}$alkyl, provided that $R^a$ is a covalent bond when $R^a$ is in a non-terminal position; and m is 1 to 9;

$R^b$ in each instance is independently H or $C_{1-10}$ alkyl optionally substituted with OH, SH, $SC_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and p is an integer ranging from 1 to 9;

e)

Formula X-e

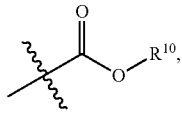

wherein $R^{10}$ is an alkyl, a polyethylene or derivative thereof or a $C_{1-10}$ alkyl wherein one or more carbons of the $C_{1-10}$ alkyl is replaced O, S, NH or $NH_2$, or an amino acid residue of A as described above via an amide linkage or an ester linkage;

or f) $R^{11}$ is selected from the group consisting of substituted arylalkyl, a sugar, alkyl or a $C_{1-10}$ alkyl, wherein one or more carbons of the $C_{1-10}$ alkyl is replaced O, S, NH or $NH_2$, or an amino acid residue of A as described above via an amide linkage or an ester linkage.

Another aspect discloses a pharmaceutical composition containing a therapeutically effective amount of the compound of Formula I for use in treatment of cancer.

In some embodiments, the present invention provides for a kit containing the compound of Formula I or a pharmaceutical composition of the compound. In some embodiments, the kit further includes one or more additional therapeutic agents to be used in combination with the compositions comprising Formula I.

In at least some embodiments, the prodrug compounds of the present invention target a member of the soluble carrier 15 (SLC15) peptide transport family, including but not limited to the PEPT1 (Peptide transporter 1) transporter system and enhances the uptake of the cannabinoid by at least 2 folds, 3 folds, 4 folds or preferably at least 5 folds higher than the degree if the cannabinoid was being delivered in its natural form. In one embodiment, the cannabinoid is CBD. In at least one embodiment, the peptide transport system is PEPT1.

Another aspect of the patent document discloses methods of modulating GPR55 receptor at the tissue site of interest. In some embodiments, the preferred modulation is inhibiting GPR55 by administering to a patient in need of effective amounts of the compounds of Formula I and inhibiting or reducing the activation of GPR55 at the target tissue site. Another aspect discloses a method of treating cancer in a subject. The method includes administering to the subject in need a compound of Formula I or a pharmaceutical composition of the compound.

DETAILED DESCRIPTION OF THE INVENTION

Figure 1:
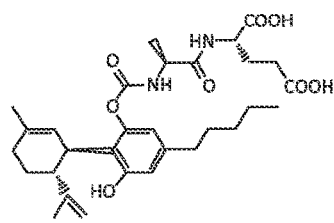
FIG. 1 shows Compound A Inhibits the Growth of the human pancreatic tumor cell line HPAF-11.
Figure 1:
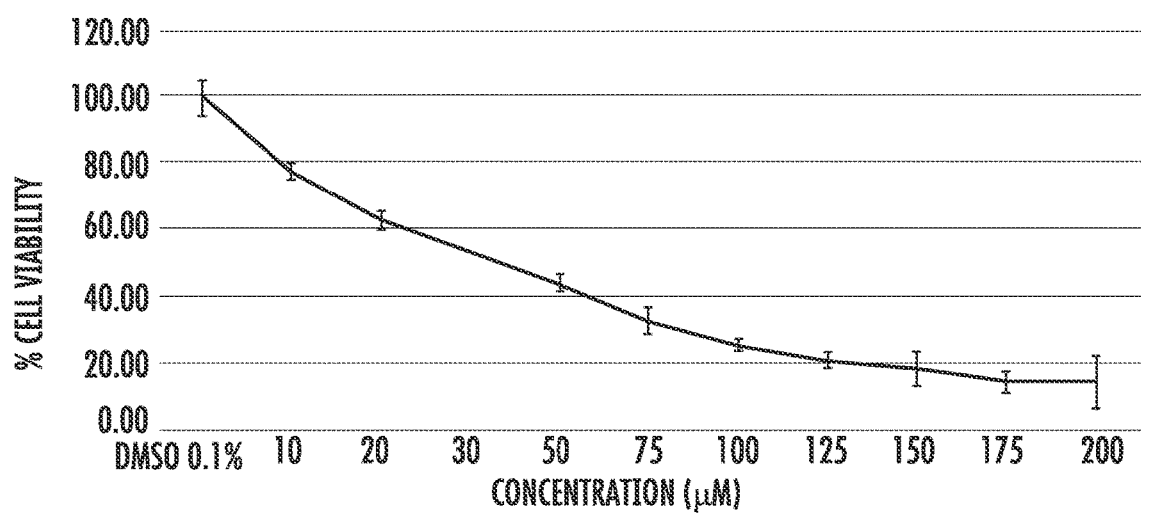

Various embodiments of this patent document discloses prodrugs of cannabidiol (CBD) and methods of administering a PEPT1-targeted cannabinoid prodrug to patient in need of such treatment. In at least one aspect, the present invention is directed to methods of inhibiting GPR55 and treating cancers in patients in need. Advantages of the prodrugs include enhanced permeability, stability, and/or excellent bioavailability after oral administration. The prodrugs can be activated by endogenous or exogenous enzymes, proteins, or suitable biological conditions.

Some examples of the present disclosure will now be described more fully hereinafter with reference to the exemplified embodiments. Indeed, various aspects of the disclosure may be embodied in many different forms and should not be construed as limited to the examples set forth herein. Rather, these examples are provided so that this disclosure will be thorough and complete and will fully convey the scope of the disclosure to those skilled in the art.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication.

The term "$C_{1-5}$ alkyl" as used herein refers to an alkyl group, liner or branched, having 1, 2, 3, 4, or 5 carbons. Nonlimiting examples include methyl, ethyl, propyl, isopropyl, butyl, isobutyl, tert-butyl, pentyl, isopentyl, etc. Similarly, the term "$C_{1-10}$ alkyl" as used herein refers to an alkyl group, liner or branched, having 1, 2, 3, 4, 5, 6, 7, 8, 9 or 10 carbons.

The term "aryl" refers to monocyclic and fused bicyclic aromatic moiety. Typically, the ring systems contain 5-12 ring member atoms. Examples of aryl groups include, without limitation, phenyl, naphthyl, anthracenyl, fluorenyl, and dihydrobenzofuranyl. "Heteroaryl" refers to optionally-substituted aromatic monocyclic and fused bicyclic heterocycles containing one or more heteroatoms selected from N, O and S in the aromatic ring system. The inclusion of a heteroatom permits inclusion of 5-membered rings as well as 6-membered rings. Examples of aryl groups include, without limitation, indolyl, azaindolyl, imidazolyl, pyrimidopyridyl, quinazolinyl, quinoxalinyl, naphthyridinyl, purinyl, imidizopyridinyl, furopyridinyl, isoindolylinyl, benzodioxinyl, dihydrobenzodioxinyl, benzothiazolyl, pyrrolopyridinyl, dihydropyrrolopyridinyl, benzoimidazolyl, imidazopyridinyl, dihydroimidazopyridinyl, tetrahydroisoindolyl, chromenyl, benzthiophene, benztriazolyl, benzfuranyl, benzoxadiazolyl, indazolyl, quinolinyl, isoquinolinyl, The term "subject" refers to a human or an animal.

The term "treating" and derivatives thereof as used herein, is meant therapeutically effective regimens to patients in need thereof. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

The term "therapeutically effective amount" or "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "specified period" and derivatives thereof, as used herein is meant the interval of time between the administration of one of the constituent drug of the inventive combination and another constituent drug. Unless otherwise defined, the specified period can include simultaneous administration. In an embodiment of a two constituent drug combination, when both compounds of the invention are administered once a day the specified period refers to timing of the administration of one drug and the other, in the relevant order during a single day. When one or both compounds of the invention are administered more than once a day, the specified period is calculated based on the first administration of each compound on a specific day. All administrations of a compound of the invention that are subsequent to the first during a specific day are not considered when calculating the specific period.

G-protein coupled receptors are active in many biologic and neurologic events including, but not limited to: addiction, anxiety, appetite, nausea, pain, sleep, vomiting. GPR55, a mammalian G-protein is expressed in areas including, but not limited to: cerebral cortex, appendix, lymph nodes, tonsils, spleen, lung, gall bladder, GI tract tissues (e.g., esophagus, salivary glands, small intestine, duodenum, rectum, colon, stomach, testis, breast, skin, etc.

Cannabinoid receptor antagonists may be used for treating a variety of diseases including inflammatory pain, reflex sympathetic dystrophy/causalgia, cataract, macular degeneration, peripheral neuropathy, entrapment neuropathy, complex regional pain syndrome, nociceptive pain, neuropathic pain, fibromyalgia, scleroderma, chronic low back pain, visceral pain, acute cerebral ischemia, pain, chronic pain, psoriasis, eczema, acute pain, post herpetic neuralgia (PHN), neuropathies, neuralgia, diabetic neuropathy, HIV-related neuropathy, nerve injury, ocular pain, headaches of various etiologies-including migraine, stroke, acute herpes zoster (shingles), pain-related disorders such as tactile allodynia and hyperalgesia, rheumatoid arthritic pain, osteoarthritic pain, back pain, cancer pain, dental pain, muscular pain, mastalgia, pain resulting from dermal injuries, fibromyalgia, neuritis, sciatica, inflammation, neurodegenerative disease, cough, broncho-constriction, irritable bowel syndrome (IBS), inflammatory bowel disease (IBD), colitis, cerebrovascular ischemia, emesis such as cancer chemotherapy-induced emesis, rheumatoid arthritis, Crohn's disease, ulcerative colitis, asthma, dermatitis, seasonal allergic rhinitis, gastroesophageal reflux disease (GERD), constipation, diarrhea, functional gastrointestinal disorders, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis, and bronchitis.

Cannabidiol (CBD) is a plant derived cannabinoid. CBD, exerts its physiologic effects through mechanisms distinct from the psycho-actives such as THC. For instance, CBD exerts an antidepressant effect by binding the G-coupled protein receptor, hydroxytryptamine serotonin receptor (HTSR). The HTSR is another member of the GPR family. Another plant cannabinoid, cannabdiolic acid (CBDA) has an even stronger affinity for HTSR. CBD or CBDA binding inhibits HTSR signaling so that stronger serotonin or analogue excitatory neurotransmitter signals are necessary. CBD has a profound antagonistic effect on GPR55, regarding its bone density and blood pressure regulation. CBD is also active with receptors in the cerebellum, jejunum and ileum. CBD derivatives have significant potential in the treatment of a variety of GPR55 associated diseases.

An aspect of this patent document provides a CBD prodrug compound of Formula I

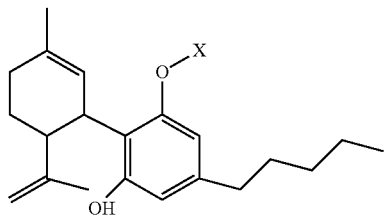

Formula I wherein:
X is a)

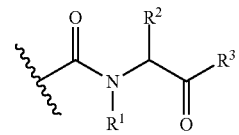

Formula X-a wherein:
R$^1$ and R$^2$ are each independently selected from the group consisting of H, C$_{1-10}$ alkyl, C$_{1-4}$ alkyl-aryl, C$_{1-4}$ alkyl-heteroaryl, each of C$_{1-10}$ alkyl, C$_{1-4}$ alkyl-aryl and C$_{1-4}$ alkyl-heteroaryl is optionally substituted with OH, SH, SC$_{1-4}$ alkyl, heteroaryl (e.g. indolyl), CONH2, COOH, NH2, NHC(NH)NH2, or aryl (e.g. imidazolyl, phenyl) optionally substituted with C$_{1-4}$ alkyl and/or OH;
and R$^3$ is selected from the group consisting of C$_{1-10}$ alkyl, C$_{1-4}$ alkyl-aryl, C$_{1-4}$ alkyl-heteroaryl, and

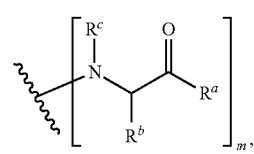

Formula Y wherein
R$^a$ in each instance is independently OH, NHC$_{1-10}$alkyl or OC$_{1-10}$alkyl, provided that R$^a$ is a covalent bond when R$^a$ is in a non-terminal position; and m is 1 to 9;
R$^b$ in each instance is independently H or C$_{1-10}$ alkyl optionally substituted with OH, SH, SC$_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and m is an integer is an integer (e.g. 1, 2, 3, 4, 5, 6, 7, 8, or 9);

b)

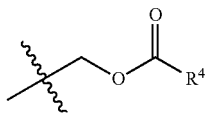

Formula X-b wherein:

$R^4$ is selected from the group consisting of H, $C_{1-10}$ alkyl, $C_{1-4}$ alkyl-aryl, $C_{1-4}$ alkyl-heteroaryl and

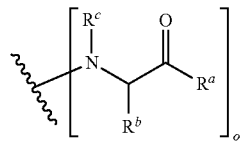

Formula Z wherein $R^a$ in each instance is OH, $NHC_{1-10}$alkyl or $OC_{1-10}$alkyl, provided that $R^a$ is a covalent bond when $R^a$ is in a non-terminal position; and m is 1 to 9;

$R^b$ in each instance is independently H or $C_{1-10}$ alkyl optionally substituted with OH, SH, $SC_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and 0 is an integer ranging from 1 to 9;

c) $(A)_n$ Formula X-c wherein: A represents an amino acid residue and n is an integer from 1 to 10, inclusive. In some embodiments, the terminal end of the amino acid residue may be presented in polar state enhancing affinity towards the target transport system. In some embodiments, the terminal end of the amino acid residue may be positively charged. In some embodiment, the terminal end of the amino acid residue may be exposed carrying a $-NH_3^+$. In some embodiment, the terminal end of the amino acid residue may be negatively charged. In some embodiments, the amino acid residue in in each instance can be the same or different and in some embodiments can be represented as

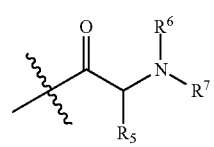

wherein:

$R^5$, $R^6$ and $R^7$ in each instance are each independently selected from the group consisting of H, $C_{1-10}$ alkyl, $C_{1-4}$ alkyl-aryl, $C_{1-4}$ alkyl-heteroaryl; wherein $R^7$ is a covalent bond to a carbonyl group if the amino acid residue is in a non-terminal position. In some embodiments, $R^5$ is H or $C_{1-10}$ alkyl optionally substituted with OH, SH, $SC_{1-4}$ alkyl, heteroaryl (e.g. indolyl), CONH2, COOH, NH2, NHC(NH)NH2, or aryl (e.g. imidazolyl, phenyl) optionally substituted with $C_{1-4}$ alkyl and/or OH. In some embodiments, $R^6$ and $R^7$ in each instance are each independently is H, or $C_{1-10}$ alkyl optionally substituted with OH, SH, $SC_{1-4}$ alkyl, heteroaryl, CONH2, COOH, NH2, or aryl; provided that $R^7$ is a covalent bond to a carbonyl group if the amino acid residue is in a non-terminal position; and n is an integer (e.g. 1, 2, 3, 4, 5, 6, 7, 8, or 9). Optionally $R^5$ and $R^6$ link up to form a 5 to 7 membered ring;

d)

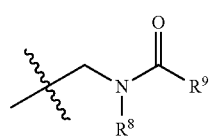

Formula X-d wherein:

$R^8$ is selected from the group consisting of H, $C_{1-10}$ alkyl, $C_{1-4}$ alkyl-aryl, $C_{1-4}$ alkyl-heteroaryl;

$R^9$ is selected from the group consisting of $C_{1-10}$ alkyl, $C_{1-4}$ alkyl-aryl, $C_{1-4}$ alkyl-heteroaryl, and

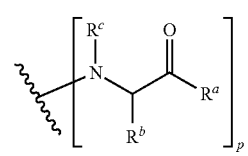

Formula P wherein $R^a$ in each instance is OH, $NHC_{1-10}$alkyl or $OC_{1-10}$alkyl, provided that $R^a$ is a covalent bond when $R^a$ is in a non-terminal position; and m is 1 to 9;

$R^b$ in each instance is independently H or $C_{1-10}$ alkyl optionally substituted with OH, SH, $SC_{1-4}$ alkyl, heteroaryl (e.g. indolyl, imidazolyl), CONH2, COOH, NH2, NHC(NH)NH2, or aryl (e.g. phenyl), wherein the heteroaryl and aryl is optionally substituted with CN, halogen, $CF_3$, $C_{1-4}$ alkyl or OH;

$R^c$ in each instance is independently selected from the group consisting of H, $C_{1-10}$ alkyl, $C_{1-4}$ alkyl-aryl, $C_{1-4}$ alkyl-heteroaryl, wherein $R^b$ and $R^c$ optionally link up to form a 5 to 7 membered ring;

and p is an integer ranging from 1 to 9;

e)

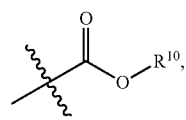

Formula X-e wherein R[10] is an alkyl, a polyethylene or derivative thereof or a $C_{1-10}$ alkyl wherein one or more carbons of the $C_{1-10}$ alkyl is replaced O, S, NH or $NH_2$, or an amino acid residue of A as described above via an amide linkage or ester linkage;
or f) R[11] is a substituted arylalkyl, a sugar, an alkyl or $C_{1-10}$ alkyl wherein one or more carbons of the $C_{1-10}$ alkyl is replaced O, S, NH or $NH_2$ or an amino acid residue of A as described above via an amide linkage or an ester linkage.

In some embodiments, the compound is OH Formula I-a,

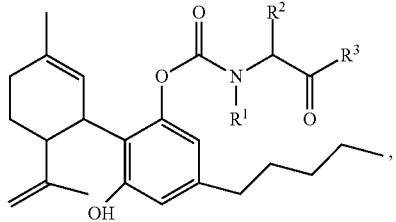

Formula I-a wherein $R^1$ and $R^2$ are each H; and $R^3$ is $C_{1-10}$ alkyl; in some embodiments, $R^2$ and $R^3$ are each an $C_{1-10}$ alkyl optionally substituted with OH, SH, $SC_{1-4}$ alkyl, heteroaryl (e.g. indolyl), CONH2, COOH, NH2, NHC(NH)NH2, imidazolyl, or aryl (e.g. phenyl) optionally substituted with $C_{1-4}$ alkyl and/or OH.

In some embodiments, the compound is represented by Formula I-a, wherein $R^3$ is

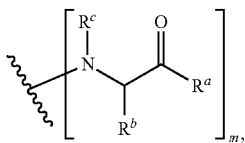

$R^1$ is H, $R^c$ is H, m is 1-4.

In some embodiments, $R^2$ is $C_{1-4}$ alkyl optionally substituted with OH, SH, SMe, or NH2; $R^a$ is OH, $R^b$ is $C_{1-4}$ alkyl optionally substituted with OH, SH, SMe, CONH2, COOH, NH2, or NHC(NH)NH2; m is 1.

In some embodiments, each

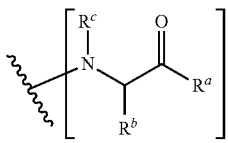

Formula Y is independently derived from lysine, leucine, isoleucine glycine, aspartic acid, glutamic acid, methionine, alanine, valine, proline, histidine, tyrosine, serine, arginine, phenylalanine or tryptophan. In some embodiment,

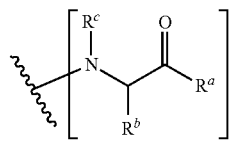

is derived from aspartic acid.

In some embodiments, each

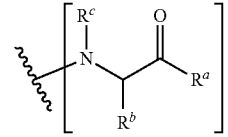

Formula Y is independently derived from glycine, aspartic acid, glutamic acid, methionine, alanine, valine, proline, histidine, tyrosine, serine, arginine, phenylalanine or tryptophan and $R^1$ and $R^2$ are each independently selected from the group consisting of H, $C_{1-10}$ alkyl, $C_{1-4}$ alkyl-aryl, $C_{1-4}$ alkyl-heteroaryl.

Exemplary embodiments for $R^3$ are as follows, when X is Formula Xa:

TABLE 1

| Entry | $R_1$ | $R_2$ | $R_3$ | Ra | Rb | Rc | m |
|---|---|---|---|---|---|---|---|
| 1 | H | H | CH3 | — | — | — | — |
| 2 | H | CH3 | C2H5 | — | — | — | — |
| 3 | H | (CH2)2CO2H | 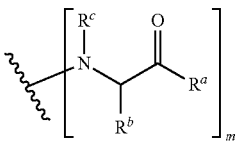 | OH | H | CH3 | 1 |
| 4 | H | CH3 | 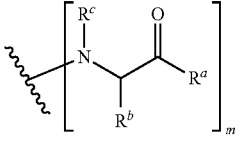 | OH | H | H | 1 |

TABLE 1-continued

| Entry | R₁ | R₂ | R₃ | Ra | Rb | Rc | m |
|---|---|---|---|---|---|---|---|
| 5 COMPOUND A | H | CH3 | [structure] | OH | (CH2)₂CO₂H | H | 1 |
| 6 | H | CH3 | [structure] | OH or bond | CH2)₂CO₂H or CH3 | H | 2 |
| 7 | H | C2H5 | [structure] | or bond | H | CH3 | 3 |
| 8 | PHENYL | CH3 | [structure] | or bond | H | CH3 | 2 |
| 9 | CH3 | CH3 | [structure] | OCH3 or bond | H | CH3 | 2 |

In some embodiments, the compound is

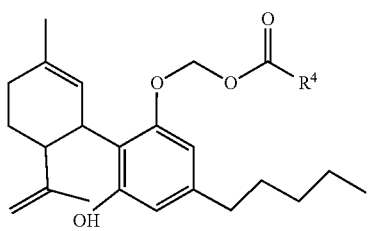

Formula I-b wherein R⁴ is H.

In some embodiments, the compound is

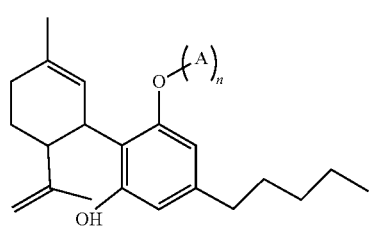

Formula I-c, which can also be represented as

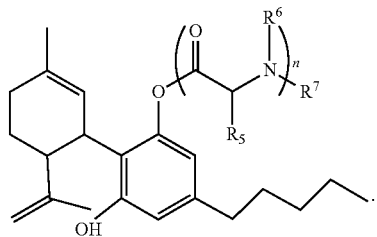

In some embodiments, n is 2 or 3. The amino acid residue refers to the structure which results from the formation of an amide bond between adjacent amino acids. The amino acid can be a synthetic or a naturally occurring amino acid. In some embodiments, the amino acid is α-amino acids. In some embodiments, the amino acid is in an L-arrangement (L-configuration). In some embodiments, the amino acid has a polar terminal ending.

In some embodiments, the amino acid residue in Formula I-c is derived independently from lysine (Lysine) (Lys), leucine (Leucine) (Leu), isoleucine (Isoleucine) (Ile), glycine (Glycine) (Gly), aspartic acid (Aspartic Acid) (Asp), glutamic acid (Glutamic Acid) (Glu), Met (methionine) (Met), alanine (alanine) (Ala), valine (valine) (Val), proline (proline) (Pro), histidine (histidine) (His), tyrosine (Tyrosine) (Tyr), serine (serine) (Ser), Nord-leucine (Norleucine) (Nor), arginine (arginine) (Arg), phenylalanine (phenylalanine) (Phe), tryptophan (tryptophan) (Trp), hydroxyproline (hydroxyproline) (Hyp), homoserine (homoserine) (Hsr), carnitine (carnitine) (Car), ornithine (ornithine) (Ort), Kana banin (Canavanine) (Cav), asparagine (asparagine) (Asn), glutamine (glutamine) (Gln), Caro Shin (Carnosine) (Can), taurine (taurine) (Tau), deujen kolrik acid (djenkolic acid) (Djk), gamma-amino butyric acid (γ-aminobutyric acid) (GABA), cysteine (Cysteine) (Cys), cystine (cystine) (dcy), sarcosine (sarcosine) (Sar), Methionine (Trenine) (Thr), derivatives and/or analogs thereof.

In some embodiments, the amino acid residue in Formula I-c is independently selected from the group consisting of Lys, is Leu, Ile, Gly, Asp, Glu, Met, Ala, Val, Pro, His, Tyr, Thr, Arg, Phe, Trp, Gln, Asn, Cys, and Ser and any combinations thereof. In some embodiments, the terminal end of the amino acid may be presented in polar state carrying a charge. In some embodiments, the terminal end of the amino acid may be an amino acid residue that is positively charged. In some embodiment, the terminal end of the amino acid residue may be exposed carrying a —$NH_3^+$. In some embodiment, the terminal end of the amino acid residue may be negatively charged. In some embodiments, the amino acid is proline, lysine or aspartic acid forming a prolyl, lysyl or aspartyl linkage or a residue thereof. In some embodiments, the compound of Formula I-c contains two amino acid residues. In some embodiments, the compound of Formula I-c contains three amino acid residues.

Exemplary embodiments for Formula X-c, wherein: A represents an amino acid residue and n is an integer from 1 to 10, are as follows:

TABLE 2

| Entry | $R_5$ | $R_6$ | $R_7$ | n |
|---|---|---|---|---|
| 9 | H | H | H | 1 |
| 10 | CH3 | H | H | 1 |
| 11 | H | CH3 | H or bond | 2 |
| 12 | CH3 | H | H or bond | 2 |
| 13 | H or (CH2)$_2$CO$_2$H | H or CH3 | H or bond | 2 |
| 14 | H or (CH2)$_2$CO$_2$H | H | H or bond | 2 |
| 15 | CH3 or (CH2)$_2$CO$_2$H | H | | |

In some embodiments, the compound of Formula I is Formula I-d:

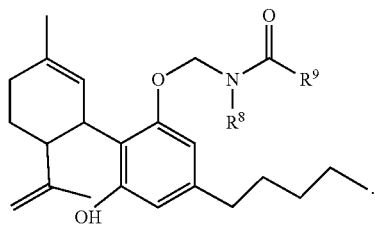

I-d

In some embodiments, the compound of Formula I is Formula I-e:

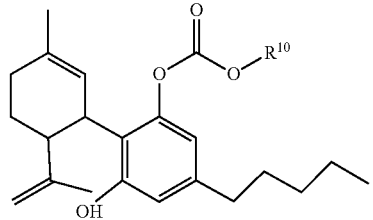

I-e

In some embodiments, the carbonate group as a whole improves the solubility of the compound. For instance, $R^{10}$ can be an alkyl with one or more carbons replaced O, S, NH or $NH_2$. Examples of $R^{10}$ include $CH_2CH_2SS\ CH_2CH_2NH_2$ and $CH_2CH_2O(CH_2CH_2)_xOC_{1-2}$alkyl (x is any integer including 1, 2, 3, 4, 5, 6, 7, 8, 9, 10 and any number greater than 10).

In some embodiments, the compound of Formula I is Formula I-f:

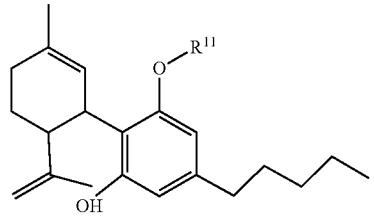

I-f $R^{11}$ is an optionally substituted arylalkyl, a sugar moiety, or $C_{1-10}$ alkyl wherein one or more carbons of the $C_{1-10}$ alkyl is replaced O, S, NH or $NH_2$. An example of the sugar moiety is

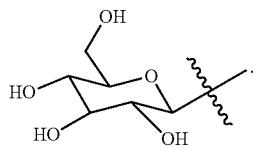 [SMILES: *C1OC(CO)C(O)C(O)C1O]

An example of the substituted arylalkyl is

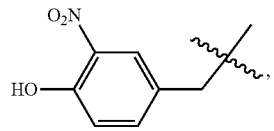

where the hydroxyl group can be glycosylated. Upon enzymatic removal of the sugar moiety, a 1-6-elimination process will reveal the active ingredient.

The compounds of Formula I may contain one or more chiral atoms, or may otherwise be capable of existing as two enantiomers and suitable pharmaceutically acceptable salts thereof. Accordingly, the compounds of this invention include mixtures of enantiomers as well as purified enantiomers or enantiomerically enriched mixtures. This principle for the encompassed scope also applies secondary agents such as "cytotoxic agent" and "molecularly targeted agent". For example, the term "cisplatin" used herein encompasses all its tautomers and mixtures of tautomers as well as pharmaceutically acceptable solvates and/or salts thereof just as same as it would be so for the term "cytotoxic agent" when in combination with the compound of Formula I.

In exemplary embodiments for any of the compounds disclosed herein, the stereochemistry may be one of the following:

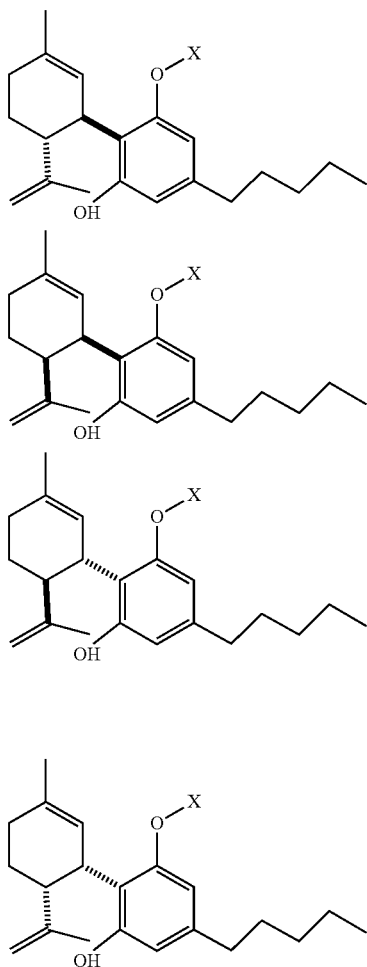

In further exemplary embodiments for any of formula X-a of the compounds disclosed herein, the stereochemistry may be one of the following:

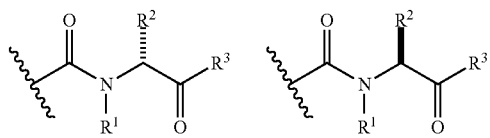

In further exemplary embodiments for any A of formula X-c of the compounds disclosed herein, the stereochemistry may be one of the following:

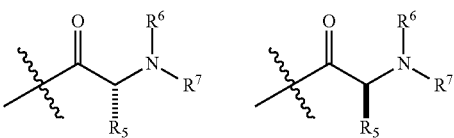

For any of the amino acid residue moiety (e.g. $R^3$ in formula X-a and A in Formula X-c), the stereochemistry may be R or S. In some embodiments, the amino acid residue moiety is derived from natural amino acid. In some embodiments, the amino acid residue moiety is derived from essential amino acid.

The compounds of the invention may form a solvate which is understood to be a complex of variable stoichiometry formed by a solute (in this invention, the solute can be the compound of Formula I or a salt thereof with a cytotoxic agent or a salt thereof and/or a molecularly targeted agent or a salt thereof) and a solvent. Such solvents for the purpose of the invention may not interfere with the biological activity of the solute. Examples of suitable solvents include, but are not limited to, water, methanol, dimethyl sulfoxide, ethanol and acetic acid. Suitably the solvent used is a pharmaceutically acceptable solvent. Suitably the solvent used is water.

In some embodiments, the process of synthesizing such prodrugs may follow chemical steps that are well known (see Vig et al. Pharm Res 2003; 20; 1381-8) including the step of protecting the amino acid moiety with a protecting agent such as tert-butyloxycarbonyl (boc), employing suitable solvent systems such as N, N. dicyclohexylcarbodiimide, or N, N dimethylaminopyridine, trifluroacetic acid (TFA), or DMF, and employing a suitable separation step to isolate the amino acid cannabinoid prodrug. In preferred embodiment, the purity of the prodrug compound ranges between 90% to 99%.

Various synthesis approaches can be applied to the compounds disclosed herein. For instance, for compounds having a carbamate moiety where X is formula X-a, the carbamate moiety can be constructed by alcoholysis of a chloroformamide, reaction between a chloroformate and an amine, or reaction between an isocyanate and an alcohol. For compounds having an acyloxymethyl ether moiety where X is formula X-b, the synthesis can be accomplished by reacting a halo-methyl ether with an acid in the presence of a base. Similarly, for compounds having an N-amidomethyl ether moiety where X is formula X-d, the reaction between a halo-methyl ether and a primary amide or a secondary amide in the presence of a base will provide the desired compounds. For compounds having a multi-peptide moiety where X is formula X-c, the amide bond formation can be facilitated with coupling agents such as dicyclohexylcarbodiimide (DCC) and diisopropylcarbodiimide (DIC). Compounds of Formula I-e having a carbonate linkage can be prepared by for example reacting an ester having an activated carbonyl with an alcohol. An ether can be prepared by reacting a phenol with an alkyl halide in the presence of a base. Various other approaches can also be employed for any of the compounds disclosed herein. Exemplary synthesis approaches are provided in references such as Modern Organic Synthesis: An Introduction, 2nd Edition, Wiley, 2017 and Organic Synthesis: The Disconnection Approach 2nd Edition, Wiley, 2008.

Figure 9:
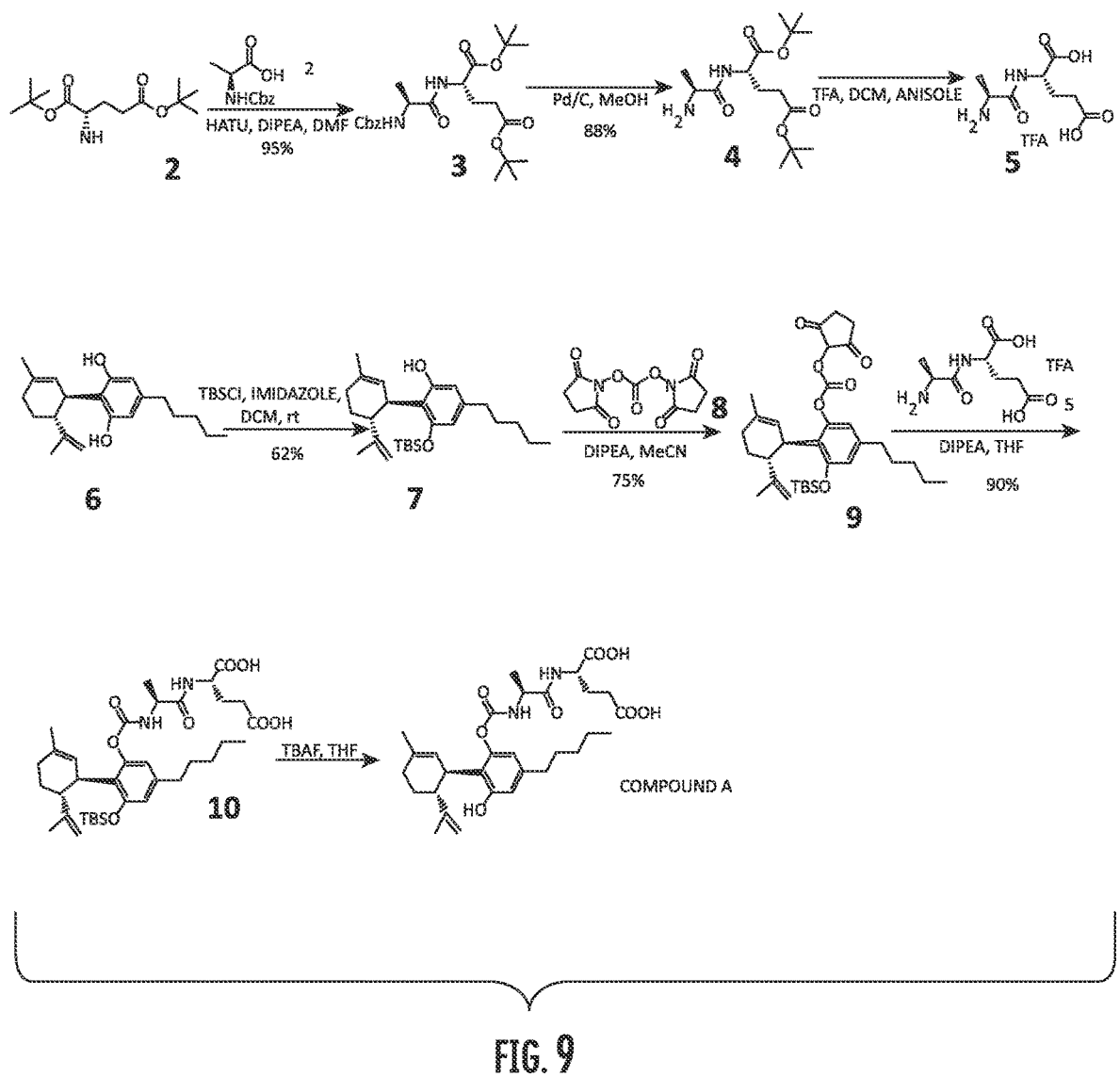
FIG. 9 shows the synthesis of Compound A.
Figure 10:
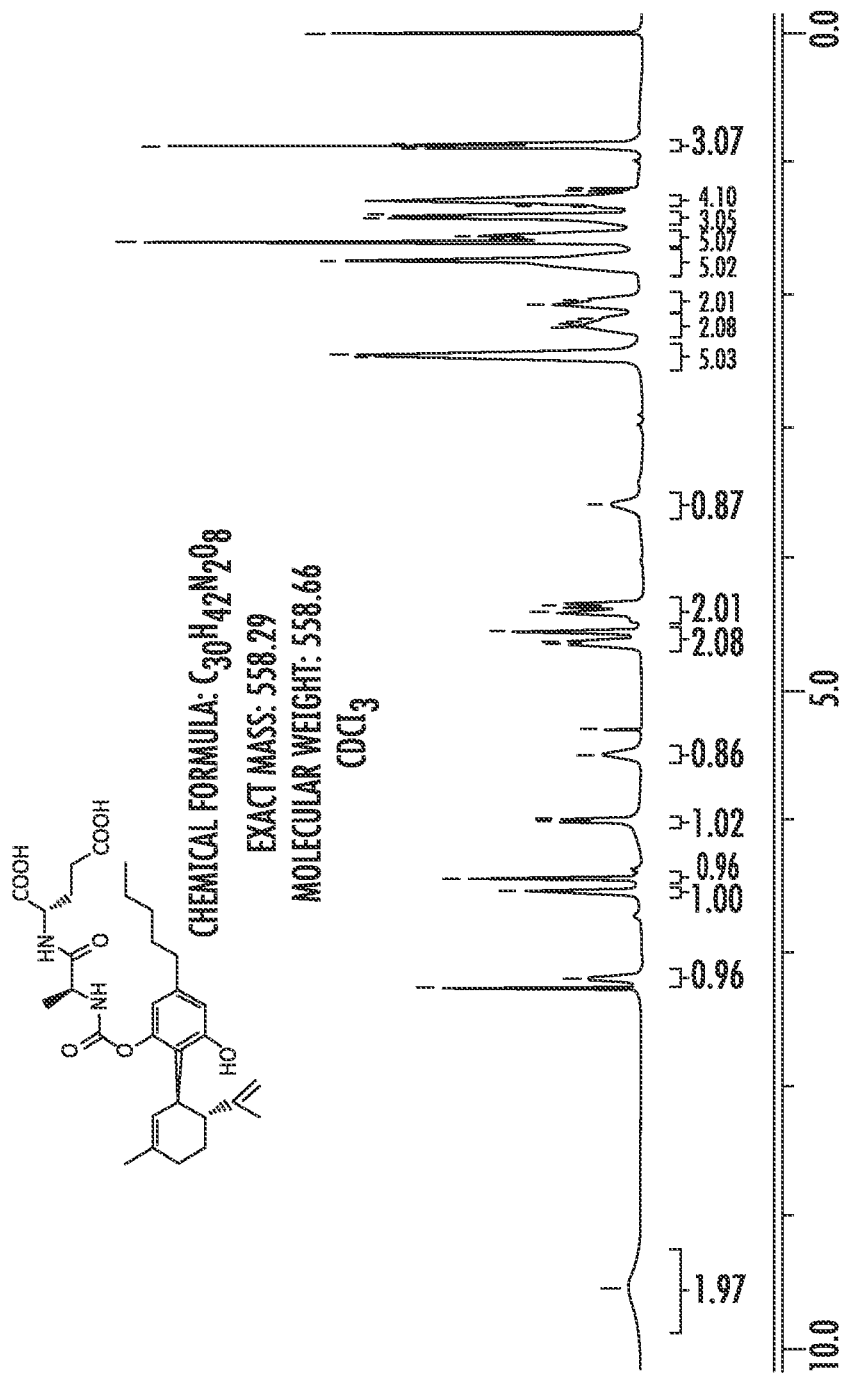
FIG. 10 shows the NMR characterization of Compound A.

In at least some embodiments, the present invention is directed to methods of synthesizing the molecules of Table 1 following the following general synthetic process steps as shown in FIG. 9. In at least one embodiment, COMPOUND A is manufactured according to the following process steps:

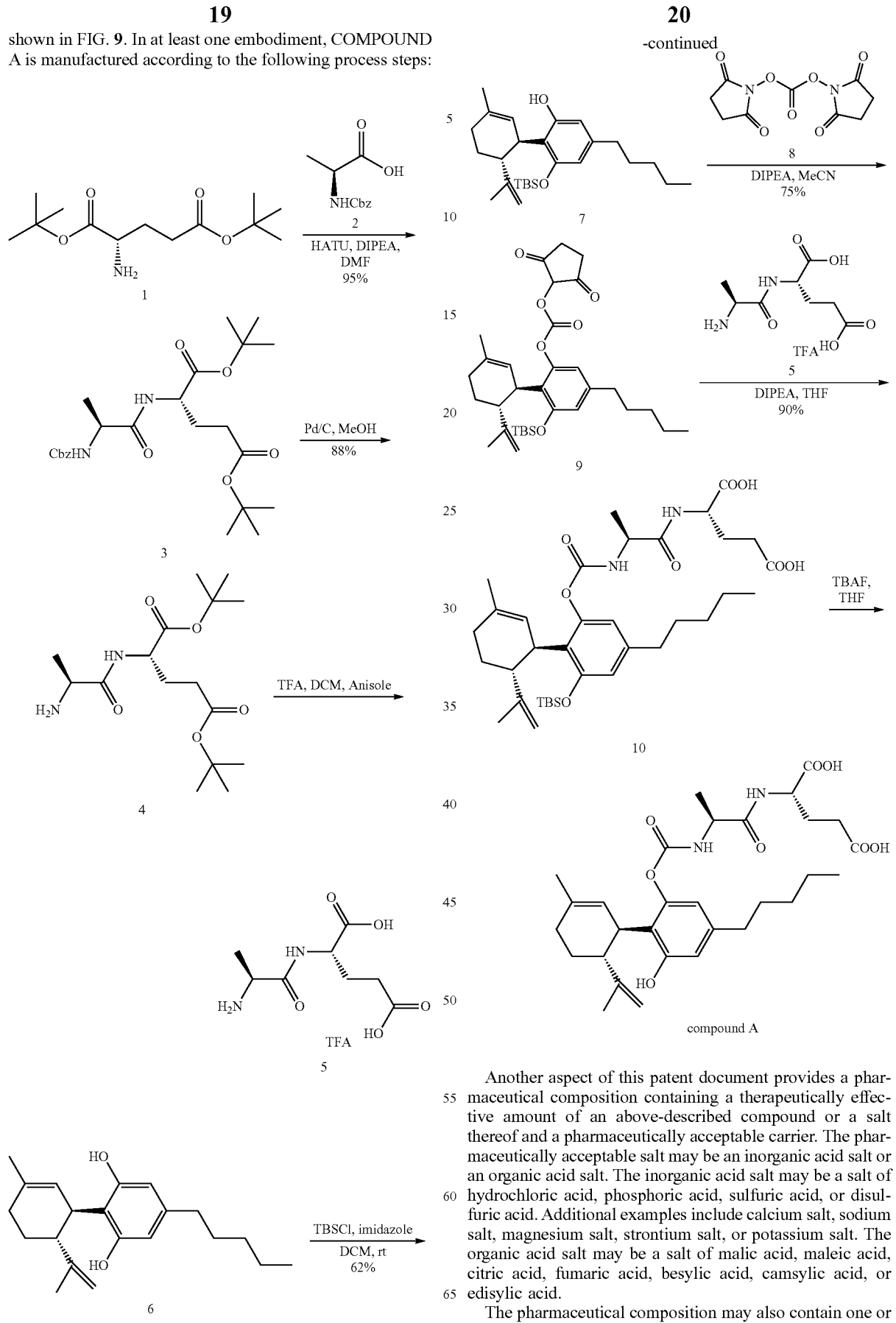

compound A

Another aspect of this patent document provides a pharmaceutical composition containing a therapeutically effective amount of an above-described compound or a salt thereof and a pharmaceutically acceptable carrier. The pharmaceutically acceptable salt may be an inorganic acid salt or an organic acid salt. The inorganic acid salt may be a salt of hydrochloric acid, phosphoric acid, sulfuric acid, or disulfuric acid. Additional examples include calcium salt, sodium salt, magnesium salt, strontium salt, or potassium salt. The organic acid salt may be a salt of malic acid, maleic acid, citric acid, fumaric acid, besylic acid, camsylic acid, or edisylic acid.

The pharmaceutical composition may also contain one or more physiologically acceptable surface active agents, additional carriers, diluents, excipients, smoothing agents, suspension agents, film forming substances, and coating assistants, or a combination thereof. Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetatemethacrylate copolymer as a derivative of polyvinyl may be used as suspension agents; and plasticizers such as ester phthalates and the like may be used as suspension agents.

The pharmaceutical composition may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmaceutical arts.

Another aspect of this patent document provides a kit containing the above-described compound or pharmaceutical composition. In some embodiments, the kit may contain one or more secondary therapeutic compounds/agents. The components of the kit may be provided in a form which is suitable for sequential, separate and/or simultaneous administration. In some embodiments, the compounds can be administered simultaneously, wherein at least two of the compounds can be physically separate or in a single pharmaceutical composition, such as a tablet. In some embodiments, the compounds are not administered simultaneously, the combination kit will contain the compound of Formula I and the other constituent drug(s) or pharmaceutically acceptable salts or solvates thereof, in separate pharmaceutical compositions. The kit can comprise the compound of Formula I and the other constituent drug(s) or pharmaceutically acceptable salts or solvates thereof in separate pharmaceutical compositions in a single package or in separate pharmaceutical compositions in separate packages.

In some embodiments, the secondary agent in the kit is a cytotoxic agent, which has a cytotoxic effect on a cell. A cytotoxic effect refers to the depletion, elimination and/or the killing of target cells (i.e., tumor cells). The cytotoxic agent may be at least one selected from the group consisting of an antimetabolite, a mitotic inhibitor, an alkylating agent, a platinum-based antineoplastic, an antibody based EGFR inhibitor, an antibody based HER2/3 inhibitor, an angiogenesis inhibitor, a mTOR inhibitor, a CDK4 and CDK6 inhibitor or an aromatase inhibitor. The combination may include at least two cytotoxic agents. For example, the combination may include at least 2, at least 3, or at least 4 selected from the group consisting of an antimetabolite, a mitotic inhibitor, an alkylating agent, an angiogenesis inhibitor and a platinum-based antineoplastic drug, or all of them.

The antimetabolite may be a drug that inhibits DNA synthesis in cells by suppressing formation of purines or pyrimidines, which are bases of a nucleotide. In one embodiment, the antimetabolite may be selected from the group consisting of Capecitabine, 5-Fluorouracil, Gemcitabine, Pemetrexed, Methotrexate, 6-Mercaptopurine, Cladribine, Cytarabine, Doxifludine, Floxuridine, Fludarabine, Hydroxycarbamide, decarbazine, hydroxyurea, and asparaginase. In a more specific embodiment, the antimetabolite is a base analog, with the term base analogs herein including nucleotide and nucleoside analogs in addition to purine base analogs such as 5-fluorouracil.

The mitotic inhibitor may be a microtubule-destabilizing agent, a microtubule-stabilizing agent, or a combination thereof. The mitotic inhibitor may be selected from taxanes, vinca alkaloids, epothilone, or a combination thereof. In a specific embodiment, the mitotic inhibitor is a taxane, for example including but not limited to, paclitaxel, docetaxel and cabaitaxel. In another specific embodiment, the mitotic inhibitor is a vinca alkaloid or its derivative, for example including but not limited to, vinblastine, vincristine, vinflunine, vinorelbine, vincaminol, vinburnine, vineridine and vindesine.

The mitotic inhibitor may be selected from BT-062, HMN-214, eribulin mesylate, vindesine, EC-1069, EC-1456, EC-531, vintafolide, 2-methoxyestradiol, GTx-230, trastuzumab emtansine (T-DM1), crolibulin, D1302A-maytansinoid conjugates IMGN-529, lorvotuzumab mertansine, SAR-3419, SAR-566658, IMP-03138, topotecan/vincristine combinations, BPH-8, fosbretabulin tromethamine, estramustine phosphate sodium, vincristine, vinflunine, vinorelbine, RX-21101, cabazitaxel, STA-9584, vinblastine, epothilone A, patupilone, ixabepilone, Epothilone D, paclitaxel, docetaxel, DJ-927, discodermolide, eleutherobin, and pharmaceutically acceptable salts thereof or combinations thereof.

The angiogenesis inhibitors are substances that inhibits the growth of new blood vessels (angiogenesis). Some angiogenesis inhibitors are endogenous and a normal part of the body's control and others are obtained exogenously through pharmaceutical drugs or diet. In at least one embodiment, the angiogenesis inhibitors include bevcizumab, sunitinib, sorafenib or pazopatinib.

The platinum-based antineoplastic drug may be selected from the group consisting of Cisplatin, Carboplatin, Dicycloplatin, Eptaplatin, Lobaplatin, Miriplatin, Nedaplatin, Oxaliplatin, Picoplatin, and Satraplatin.

As used herein, a "molecularly targeted agent" is a substance that interferes with the function of a single molecule or group of molecules, preferably those that are involved in tumor growth and progression, when administered to a subject. Non-limiting examples of molecularly targeted agent of the present invention include signal transduction inhibitors, modulators of gene expression and other cellular functions, immune system modulators, antibody-drug conjugates (ADCs), and combinations thereof.

The molecularly targeted agent may be selected from epidermal growth factor receptor family inhibitors (EGFRi), mammalian target of rapamycin (mTOR) inhibitors, immune checkpoint inhibitors, anaplastic lymphoma kinase (ALK) inhibitors, B-cell lymphoma-2 (BCL-2) inhibitors, B-Raf inhibitors, cyclin-dependent kinase inhibitors (CDKi), such as the CDK4/CDK6 inhibitor, palbociclib, ERK inhibitors, histone deacetylase inhibitors (HDACi), heat shock protein-90 inhibitors (HSP90i), Janus kinase inhibitors, mitogen activated protein kinase (MAPK) inhibitors, MEK inhibitors, such as the MEK1/MEK2 inhibitor trametinib, poly ADP ribose polymerase (PARP) inhibitors, phosphoinositide 3-kinase inhibitors (PI3Ki), Ras inhibitors, sodium-glucose linked transporter (SGLT) inhibitors, PD-1 checkpoint inhibitors such as nivolumab (OPDIVO®), pembroluzimab (KEYTRUDA), atezolizumab, durvalumab, cempilimab, avelumab and any combinations thereof.

Suitable sodium-glucose linked transporter (SGLT) inhibitors, also known as sodium-dependent glucose cotransporter inhibitors, include inhibitors of sodium/glucose cotransporter 1 (SGLT1).

The molecularly targeted agent may be selected from ado-trastuzumab emtansine (T-DM1), alemtuzumab, cetuximab, ipilimumab, ofatumumab, panitumumab, pertuzumab, rituximab, tositumomab, 131I-tositumomab, trastuzumab, brentuximab vedotin, denileukin diftitox, ibritumomab tiuxetan, axitinib, bortezomib, bosutinib, cabozantinib, crizotinib, carfilzomib, dasatinib, erlotinib, gefitinib, imatinib mesylate, lapatinib, nilotinib, pazopanib, ponatinib, regorafenib, ruxolitinib, sorafenib, sunitinib, tofacitinib, vandetanib, vemurafenib, alitretinoin, bexarotene, everolimus, romidepsin, temsirolimus, tretinoin, vorinostat, nivolumab, pembroluzimab, atezolizumab and pharmaceutically acceptable salts thereof or combinations thereof.

The EGFR inhibitors may be selected from erlotinib, gefitinib, lapatinib, canetinib, pelitinib, neratinib, (R,E)-N-(7-chloro-1-(1-(4-(dimethylamino)but-2-enoyl)azepan-3-yl)-1H-benzo[d]imidazol-2-yl)-2-methylisonicotinamide, Trastuzumab, Margetuximab, panitumumab, matuzumab, necitumumab, pertuzumab, nimotuzumab, zalutumumab, cetuximab, icotinib, afatinib, and pharmaceutically acceptable salt thereof. In one embodiment the EGFR inhibitor may be an antibody based EGFR inhibitor such as cetuximab and in another embodiment, it is necitumumab and yet in another embodiment it is pantitumumab. The molecularly targeted agent may be an anti-EGFR family antibody or a complex including the anti-EGFR family antibody. The anti-EGFR family antibody may be an anti-HER1 antibody, an anti-HER2 antibody, or an anti-HER4 antibody.

The kit can also be provided with instruction, such as dosage and administration instructions. Such dosage and administration instructions can be of the kind that is provided to a doctor, for example by a drug product label, or they can be of the kind that is provided by a doctor, such as instructions to a patient.

The compounds of Formula I or combinations thereof with one or more additional agents can be incorporated into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. One or more of flavoring agent, preservative, dispersing agent and coloring agent can also be present.

It should be understood that in addition to the ingredients mentioned above, the formulations may include other agents conventional in the art having regard to the type of formulation in question, for example those suitable for oral administration may include flavoring agents.

The Solute Carrier 15 (SLC15) family of peptide transporters, alias $H^+$-coupled oligopeptide cotransporter family, is a group of membrane transporters known for their key role in the cellular uptake of di- and tripeptides (di/tripeptides). In at least one embodiment, the present invention is directed to methods of enhancing the transport mediated uptake of the present compounds to the desired tissue. In at least one embodiment, such transport system include but are not limited to PEPT1, PEPT2, PHT1, PHT2, a related subfamily or any combination thereof. In some embodiments, the present invention enhances the uptake of the cannabinoid by at least 2 folds, 3 folds, 4 folds or preferably at least 5 folds higher than the degree if the cannabinoid was being delivered in its natural form.

Another aspect of the present invention is directed to methods of enhancing PEPT1-mediated uptake of the active moiety in tissues to that express PEPT1. PEPT1 has been described to have nutritional importance because of its role in intestinal absorption of small peptides from the diet and in reabsorption of the peptide bound amino nitrogen from glomerular filtrate in the kidneys. (See Hu et al, Mole. Pharmaceutics 2008, 5, 1122-1130). PEPT1 also plays a significant role in transporting therapeutic agents into cells. In some embodiments, the presently described prodrugs enhances the uptake of its active cannabinoid by at least 2 folds, 3 folds, 4 folds or preferably at least 5 folds higher than the degree if the cannabinoid was being delivered in its natural form. In one embodiment, the cannabinoid is CBD. In at least one aspect of the present invention, the prodrug compounds of the present invention the inventor propose a modified ALA-ASP—cannabinoid molecule and ALA-Glu benzyl ester of the cannabinoid molecule as a prodrug that has an affinity for the PEPT1. In one embodiment, the cannabinoid is THC or CBD or salts thereof.

Another aspect of the patent document provides a method of inhibiting GPR55, comprising contacting the GPR55 with a therapeutically effective amount of the compound of Formula I, salts thereof or a pharmaceutical composition containing such compounds. GPR55 is a G-protein coupled receptor and is activated by cannabinoids (CBs) and non-CB with LPI (lysophosphatidylinositol) believed to be its putative endogenous ligands and potent agonist. It is a phospholipid receptor that is expressed in the bone marrow, spleen, immune cells, endothelial cells, central nervous system, vasculature, placenta and throughout the intestine (duodenum, jejunum, ileum and colon) and is also found in cancer tissues and cancer cell lines. Recent studies have shown that it colocalizes with CB1 and CB2 and can work independently or form heteromers modulating downstream signaling based on activation or inhibition of these receptors. Moreover, CBD has been shown to impact cancer through four key pathways ERK, PI3K, ROS and MAPK pathways. To that end, in at least one embodiment, the use of CBD in treating cancer or improving patient's outcome in population at risk of developing resistant to the first line of cancer treatment is also contemplated. In at least one embodiment, the present invention, use of the present novel compounds provides a longer duration of time to which a patient may observe drug resistance to the first line treatment as compared to those patients only receiving the first line treatment.

GPR55 is overexpressed in several types of cancer such as pancreatic cancer, colorectal cancer, triple negative breast cancer, gliobastoma which increases cell proliferation and tumor growth while its inhibition reduces these properties, increases cell adhesion, promotes migration/invasion (indicators of metastasis), increases cell division. Activation of GPR55 results in an increase in intracellular Ca2+ and ERK phosphorylation. It has been shown that upon GPR55 activation, nuclear factor of activated T-cells (NFAT) implicated in tumor migration, nuclear factor k-light chain-enhancer of activated B cells (NFkB), and MAP kinases (p38 and ERK ½ MAK) are activated. Studies have suggested that inhibition of GPR55 has therapeutic effect in a number of disease areas including obesity, diabetes mellitus, inflammatory and neuropathic pain, vasculature, cancer, inflammation, gastrointestinal tract disease, and bone disease. Overall, clinical studies indicate that higher GPR55 expression is correlated with reduced patient survival.

Because CBD exhibits inhibitive effect against GPR55, the prodrug compound of CBD is also expected to be effective against the same target. Further, it has been demonstrated that pharmacological inhibition of GPR55 with CBD increases effects of gemcitabine in cancer treatment. In other embodiments, CBD can be used in combination with GRP55 inhibitors to delay, prevent or minimize GRP55 inhibitor drug resistance at the receptor site. To that end, at least one embodiment is directed to the use of CBD in prolonging or maximizing the duration of GPR55 therapy as compared to the administration of such drug alone, by mitigating or reducing the risk of drug therapy resistance at the site of interest. Without being bound to any particular theory, it is postulated that GPR55 antagonism blocks metastatic behavior (adhesion, invasion and migration) of cancer cells and arrest of cancer cells in liver tissue. In some embodiments, the GPR55 is overexpressed in tumor cells in a subject, which is an animal or a human.

In some embodiments, the present invention is directed to treating cancer or killing tumor cells wherein the cancer is selected from the group consisting of hepatocellular cancer, lung cancer (including Non-Small Cell Lung Cancer), pancreatic cancer, gastric cancer, squamous cell cancer, ovarian cancer, prostate cancer, colorectal cancer, ovarian cancer, cholangiocarcinoma, glioblastomas, leukemia (including Chronic Lymphocytic Leukemia), breast cancer including triple-negative. In some embodiments, the cancer is pancreatic ductal adenocarcinoma or colorectal cancer. In some embodiments, the tumor cells are screened for their respective cancer specific biomarkers. In some embodiments, the tumor cells may be screened for GPR 55 and PEPT1 expression.

In at least one embodiment, the present methods are directed to administering the instant prodrug compounds to patients in need to modulate and/or inhibit GPR55 to increase survival of such patients. In at least some embodiments, the present methods of treatment is directed to detecting patients degree of GPR 55 expression, administering a prodrug compound comprising a cannabinoid moiety, and inhibiting GPR55 and reducing pancreatic cancer cell proliferation, and/or enhancing the antitumor effects of the cannabinoid by prolonging the survival of patients in need of such treatment. In one embodiment, the cannabinoid is a THC, CBD, salts thereof or any combinations thereof. In some embodiments, the present invention is directed to a method for treating a subject suffering from a cancer wherein the GPR 55 is overexpressed at its cellular level, comprising obtaining an biological sample from the subject, determining the degree of GPR 55 expression at the cellular level from the biological sample, and applying the prodrug to said biological sample to reduce or inhibit GPR 55 activity.

Another aspect of the patent document provides a method of treating a cancer in subject. The method includes administering to the subject a therapeutically effective amount of the cannabinoid prodrug compound described herein or the pharmaceutical composition thereof. Non-limiting examples of the cancer include pancreatic cancer, squamous cell cancer, ovarian cancer, prostate cancer, colorectal cancer, ovarian cancer, cholangiocarcinoma, glioblastomas (gbm), hepatic cancer, triple-negative breast cancer. In some embodiments, the cancer is pancreatic ductal adenocarcinoma or colorectal cancer. In some embodiments, the subject is human.

In at least one embodiment, the subjects may be screened for a specific cancer biomarker. In at least one embodiment, the subject's tissue, blood or plasma samples may be analyzed independently for the degree of tissue expression of GPR 55 and PEPT1 or other cancer specific biomarkers. In at least one embodiment, the method of treating a cancer in a subject comprise identifying subjects that show over expression of a cancer specific biomarker including but not limiting to GPR55 and/or PEPT1 and administering the compounds of Formula I in subjects in need thereof.

In some embodiments, the method includes further administering a secondary agent, simultaneously or sequentially with the administration of the compound of Formula I or a pharmaceutical composition thereof. The secondary agent is as described above in the kit.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

For oral administration, the drug compound or its composition can be formulated readily by combining the compound or its composition of interest with pharmaceutically acceptable carriers well known in the art as described above. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated.

Injectable can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks' solution, Ringer's solution, or physiological saline buffer. If desired, absorption enhancing preparations may be utilized.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The therapeutically effective amount of the compound of Formula I or its pharmaceutically acceptable salt required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods. In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

In at least one embodiment, the cannabinoid of the presently described prodrugs is CBD. CBD exhibits low, dose dependent oral and oromucosal bioavailability of about 35%. CBD administration via the i.v. route overcomes these limitations and results in highest plasma CBD levels. In at least one embodiment, the effective dose is to achieve a target serum concentration of CBD ranging from about 400 ng/ml to about 1500 ng/ml. In at least one embodiment the systemid drub delivery of the CBD prodrug is in sufficient amounts to enhance drug uptake by PEPT1-expressed cell and inhibiting GPR 55.

In some embodiment, the combination of the compounds of the present invention, and a second anticancer agent such as Taxol derivatives, or Gemcitabine derivatives provides a synergistic clinical response corresponding to at least 10% improvement in targeting and killing tumor cells as compared to the second anticancer agent itself. In some embodiments, the synergistic improvement can be due to increase cellular uptake of the compound at the region of interest.

The exact formulation, route of administration and dosage for the pharmaceutical compositions can be chosen by the individual physician in view of the subject's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the subject can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician will know how and when to terminate, interrupt, or adjust administration due to toxicity or organ dysfunctions. Conversely, the attending physician will also know to adjust treatment to higher levels if the clinical response is not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

In at least some embodiments, the compounds of Tables 1 and 2 are able to provide effective inhibition of the growth of the solid tumor cell lines in a dose dependent manner. FIGS. 4-6 provides examples of at least one such compounds that can selectively target GPR55/SCL15A1 co-expressing tumors. In some embodiments, COMPOUND A provide additional advantages over other GPR55 antagonists in that it is co-targeted to SLC15A1 on the cell surface. This co-targeting may also increase the bioavailability of COMPOUND A relative to other GPR55 antagonists in vivo.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. For instance, compositions can be administered using a regimen which maintains plasma levels above the MEC for 10-90% of the time, preferably between 30-90% and most preferably between 50-90%.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

Regarding "specified period" administration, in some embodiments, during the course of treatment, the compound of Formula I or its combination with an additional agent will be administered within a specified period for at least 1, 2, 3, 5, 7, 14, or 30 day(s) in this case, the duration of time will be at least 1, 2, 3, 5, 7, 14, or 30 day(s). When, during the course of treatment, the single compound or individual constituent of a combination is administered within a specified period for over 30 days, the treatment is considered chronic treatment and will continue until an altering event, such as a reassessment in cancer status or a change in the condition of the patient, warrants a modification to the protocol.

In some embodiments, the compound of Formula I and an additional agent are administered within a "specified period" and not administered simultaneously, they are both administered within about 24, 12, 11, 10, 9, 8, 7, 6, 5, 4, 3, 2, or 1 hour(s) of each other—in this case, the specified period will be about 24 12, 11, 10, 9, 8, 7, 6, 5, 4, 3, 2, or 1 hour(s). As used herein, for an embodiment of a two constituent drug combination, the administration of the compound of Formula I and the other constituent drug in less than about 45 minutes apart is considered simultaneous administration.

In some embodiments, when the drug combination disclosed herein is administered for a "specified period", the compounds will be co-administered for a "duration of time". By the term "duration of time" and derivatives thereof, as used herein is meant that both compounds or agents disclosed herein are administered within a "specified period" for an indicated number of consecutive days, optionally followed by a number of consecutive days where only one of the component compounds is administered.

Example

MTT Cell Viability Assay with HPAF-II (Pancreatic) Tumor Cells—
Methodology
10 mM of COMPOUND A stock solution was made by dissolving the 8.2 mg of powder form of COMPOUND A in 1.468 mL of DMSO to form the stock solution. The stock solution was aliquoted to 0.6 mL microcentrifuge tubes with 20 µl of solution in each microcentrifuge tube.

MTT Assay
Pancreatic cancer cell line HPAF-II was seeded in a 96-well plate with 5000 cells/well and incubated overnight at 37° C. The next day, cells were treated triplicate by removing cell media and replaced with fresh media containing COMPOUND A alone at increasing concentrations (10 µM, 20 µM, 20 µM, 50 µM, 75 µM, 100 µM 125 µM 150 µM, 175 µM 200 µM) as well as the combination of the 10 µM of COMPOUND A and Gemcitabine at increasing concentrations (0 µM, 0.01 µM, 0.05 µM, 0.1 µM, 0.5 µM, 1 µM, 5 µM, 10 µM). Drug vehicle (DMSO, Sigma) was used as a control for the treatment. Cells were then left to grow in the presence of the drugs for the following 72 hours.

After 72 hours, the media was discarded and the cells were incubated with MTT (3-(4,5-Dimethylthiazol-2-yl)-2, 5-diphenyltetrazolim bromide) solution (5 mg/ml stock) at working concentration of 0.5 mg/ml in fresh cell growth media for 2 hours at 37° C. The reaction was stopped when the majority of the cells was stained. MTT solution was then aspirated and the plate was left to dry for several hour. Stained cells were then resuspended in 70 µl of DMSO and mixed well. The absorbance was read with the use of a plate reading spectrophotometer at the 570 nm. The CompuSyn data for the drug combination of COMPOUND A and Gemcitabine in each cell line was generated and analysed using the CompuSyn software which was set up by Dr Dorothy Chou and published by ComboSyn, Inc.

FIG. 1 shows that COMPOUND A is effective in inhibiting the growth of the human pancreatic tumor cell line HPAF-11. As shown, at concentration of 50 µM, COMPOUND A provides at least a 50% kill of the pancreatic tumor cells and at concentrations of about 175 µM, COMPOUND A is able to reduce kill more than 80% of the tumor cells.

Figure 2:
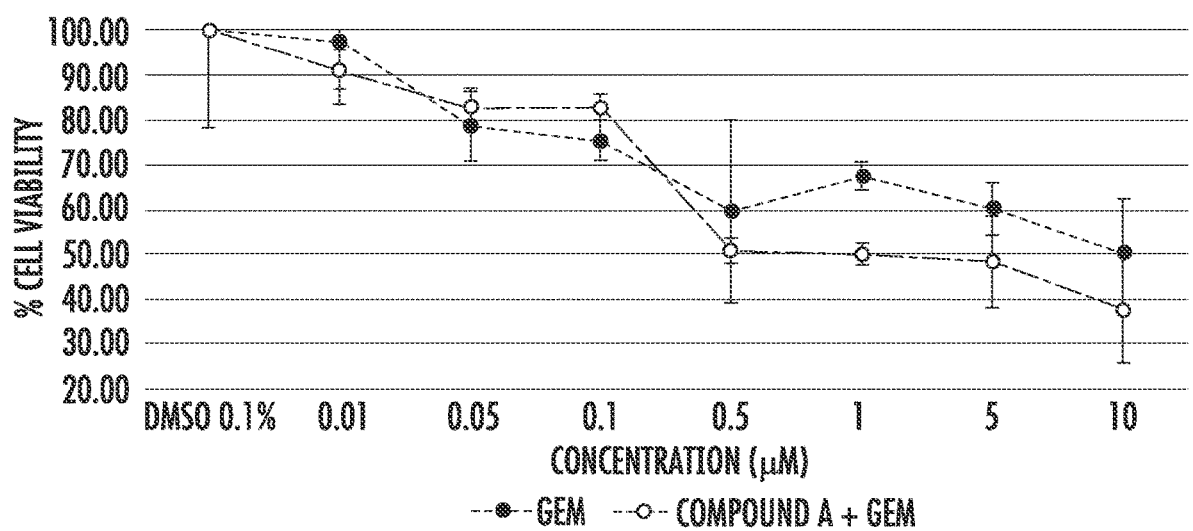
FIG. 2 shows Compound A Combined with Gemcitabine Inhibits HPAF-11 Growth Better Than COMPOUND A or Gemcitabine Alone.

When combined with Gemcitabine, a known anti cancer therapeutic approved for treating certain cancers, COMPOUND A was able to significantly the growth inhibitor effect of Gemcitabine. As provided herein FIG. 2 shows Compound A combined with gemcitabine inhibits HPAF-11 growth better by at least 10% increase in rate of the cell kill, than either Compound A or gemcitabine alone.

The combination of COMPOUND A and Gemcitabine in this example provides at least 5%, 10%, 15%, 20% or 25% superior clinical benefits as compared to Gemcitabine alone. These results suggest that COMPOUND A can provide effective anti tumor activity for such conditions as pancreatic cancer.

Cells were treated for 48 hours with indicated concentrations of COMPOUND A in DMEM containing 10% FBS.

Phosphorylation of ERK was assessed by western blot using antibodies that detect total and phospho-ERK. Actin detection was used as a loading control for total lysate protein.

Figure 3:
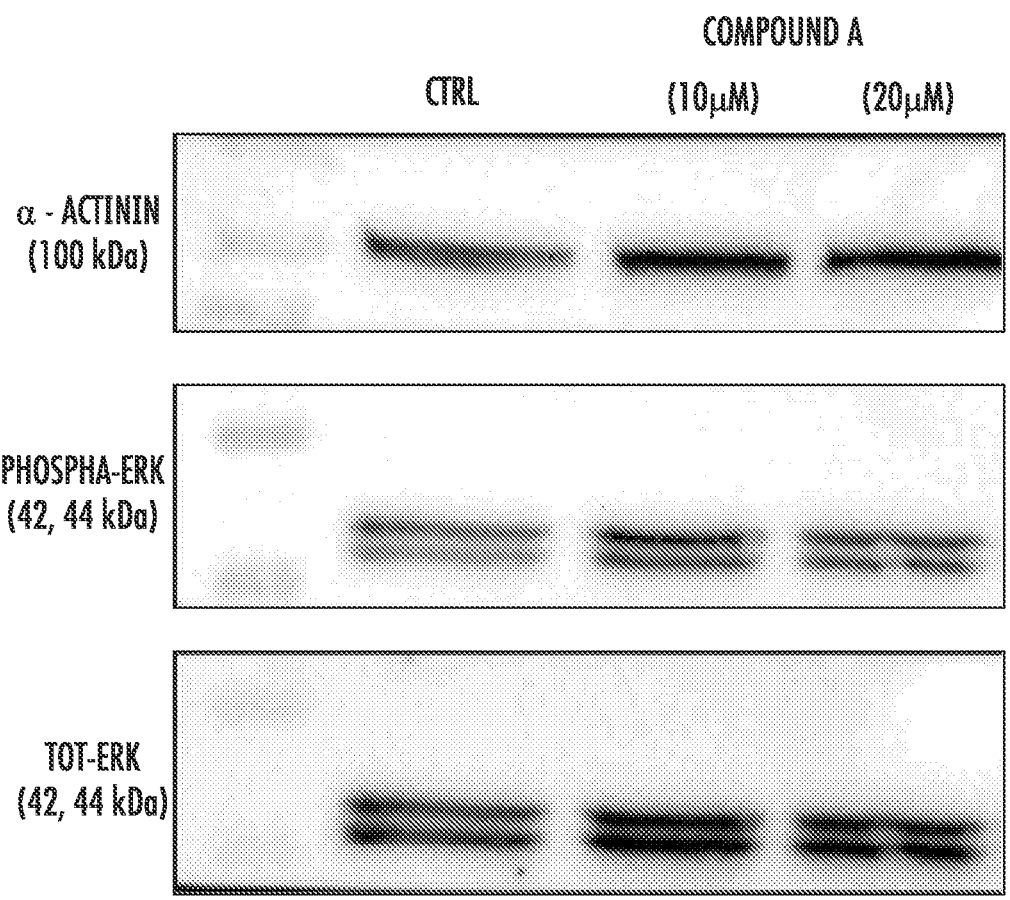
FIG. 3 shows Compound A Can Decrease Phospho-ERK levels in HPAF-11 Pancreatic Tumor Cells.

As shown in FIG. 3, COMPOUND A culture was able to effectively decrease phospho-ERK levels in tumor cells as compared to control.

CELLTITER-GLO® Cell Viability Assay (a homogeneous method of determining the number of viable cells in culture based on quantitation of the ATP present, an indicator of metabolically active cells)

Materials

MKN1 (gastric), PC3 (prostate), NCIH727 (lung), and HCT116 (colorectal) tumor cell lines; Control=0.1% DMSO To prepare 10 mM FL41 stock from powder dissolve 4.1 mg of FL41 powder into 0.74 ml DMSO-aliquot and store at −20 C until use DMSO-stock from Sigma or other suitable vendor-must be reagent or ACS grade or better.

Place 5000 cells per well (200 ul) in duplicate in their preferred media as shown in 96-well plate diagram immediately below. Reduce the final FBS (serum) concentration to 5% before adding cells to media. Incubate cells overnight and then remove old media carefully and add fresh media with 5% FBS and then either add DMSO alone, COMPOUND A alone or in combination with GEM (gemcitabine) in wells where noted at the final concentrations noted. Incubate the cells at 37 C in CO2 incubator for an additional 72 hours in presence of compounds. At the end of the 72-hour period add Promega Titerglo reagent to the wells and then measure luminescence to assess relative cell number.

In at least this embodiment, COMPOUND A is able to bind with both GPR55 and SLC15A1 (PEPT1). It selectively targets cancer cells that co-express these two receptors. Published cell line RNAseg results reported that several human tumor cell lines can co-express these two receptors at high levels. The results here show that a subset of these human tumor cell lines tested co-express the GPR55 and SLC15A1 protein as determined by western blotting. When looking at the effect of COMPOUND A alone on human tumor cells, the results showed that, COMPOUND A was able to inhibit the growth of HPAFII (pancreatic), MKN1 (gastric), HCT116 (colorectal), H727 (lung) and PC3 (prostate) tumor cell lines as compared to control. Despite a concentration dependent inhibition, COMPOUND A is able to effectively inhibit the growth of cell line in each of the above mentioned cell lines.

Figure 4A:
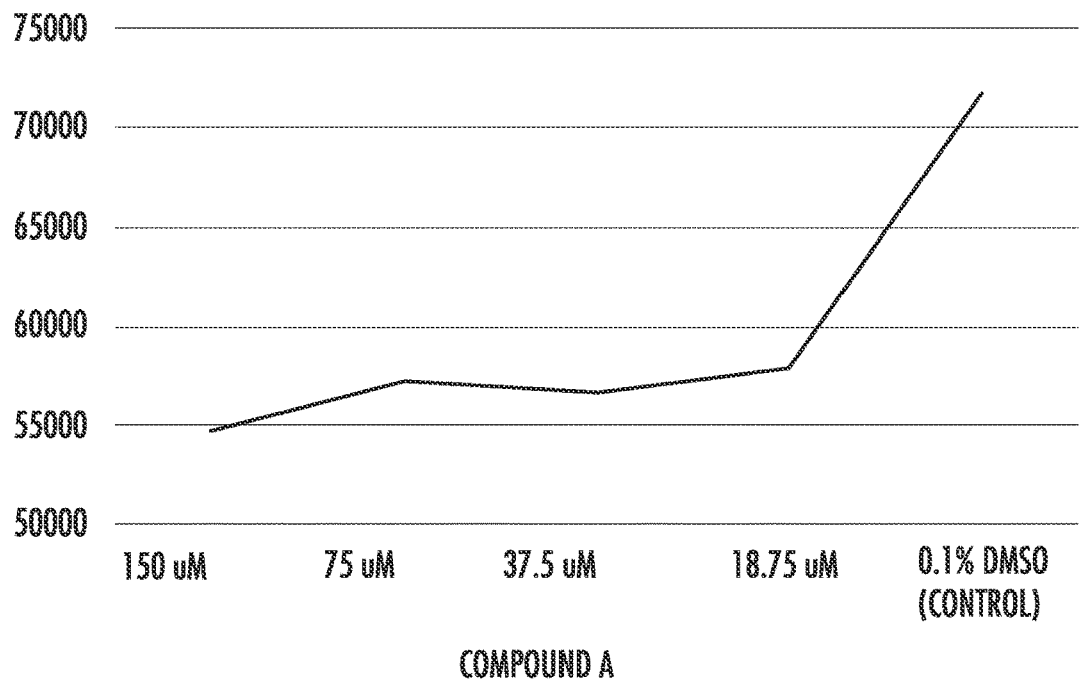
FIGS. 4(a) and 4(b) show Compound A inhibits the growth of human mkn1 gastric tumor cells.
Figure 4B:
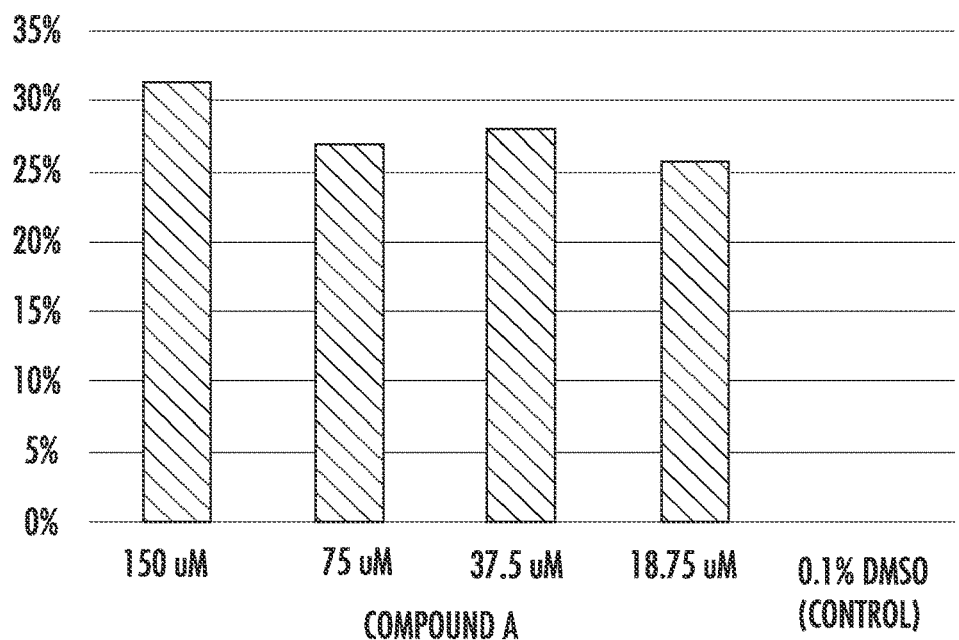
Figure 5A:
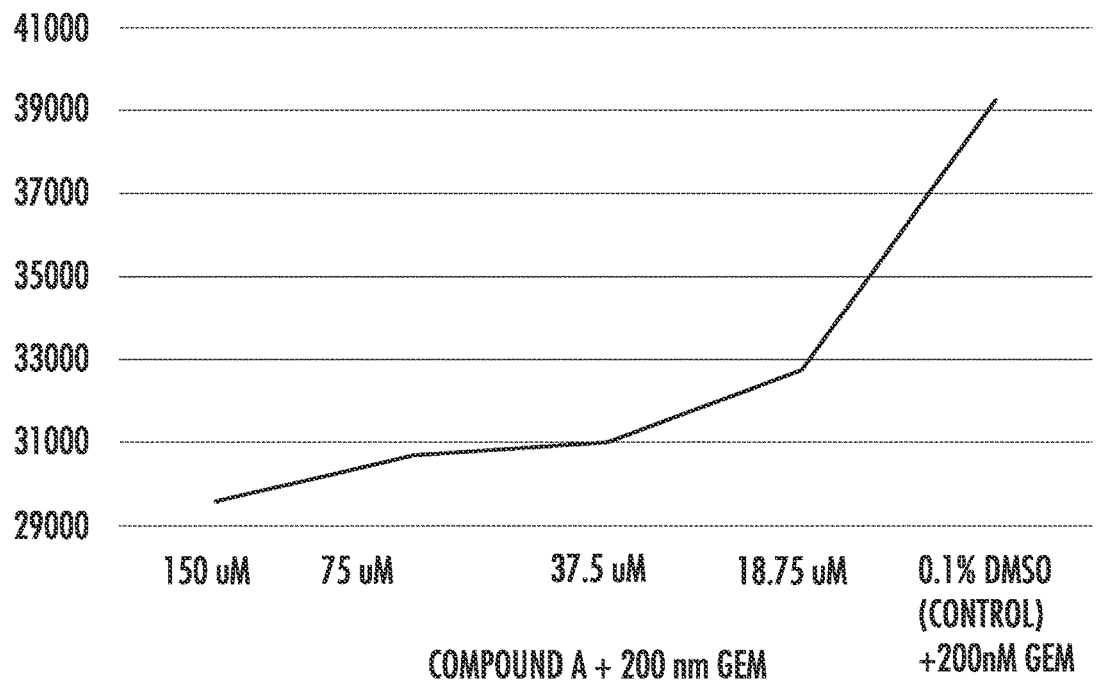
FIGS. 5(a) and 5(b) show Compound A potentiates gemcitabine growth inhibition of human mkn1 gastric tumor cells.
Figure 5B:
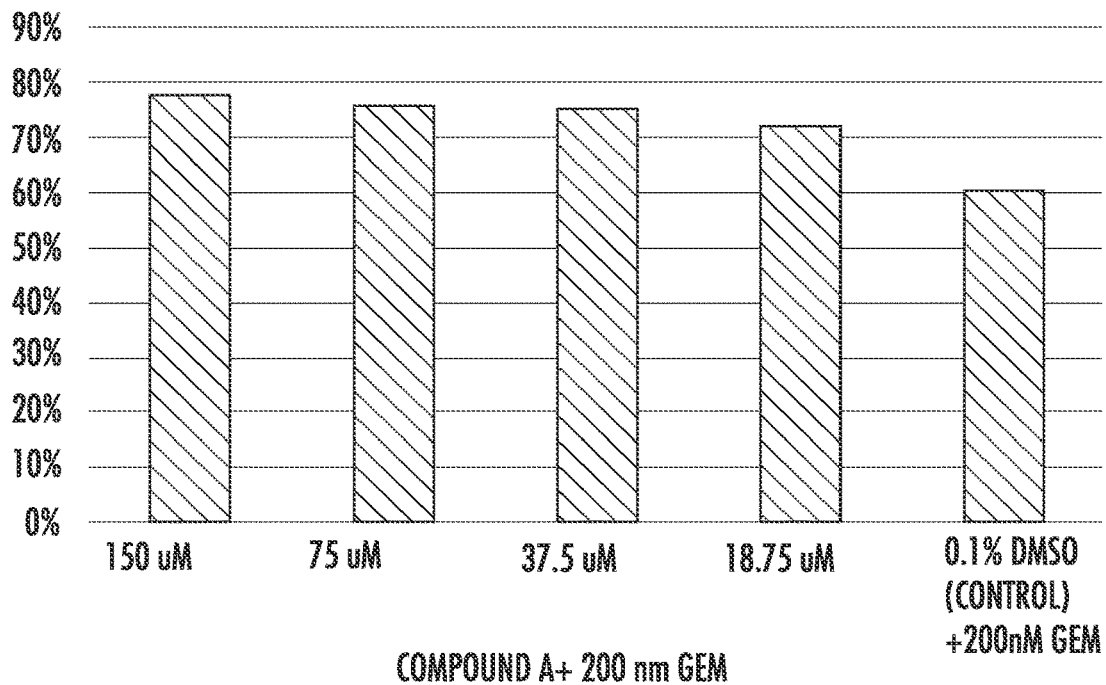
Figure 6A:
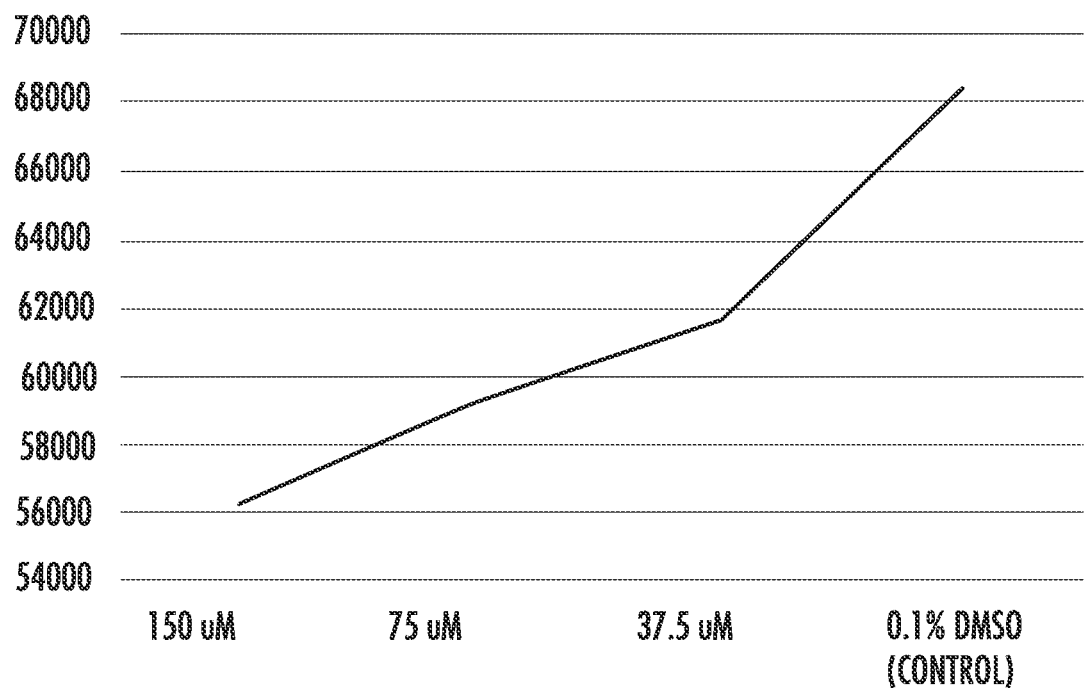
FIGS. 6(a) and 6(b) show compound A inhibits the growth of human hct116 colorectal tumor cells.
Figure 6B:
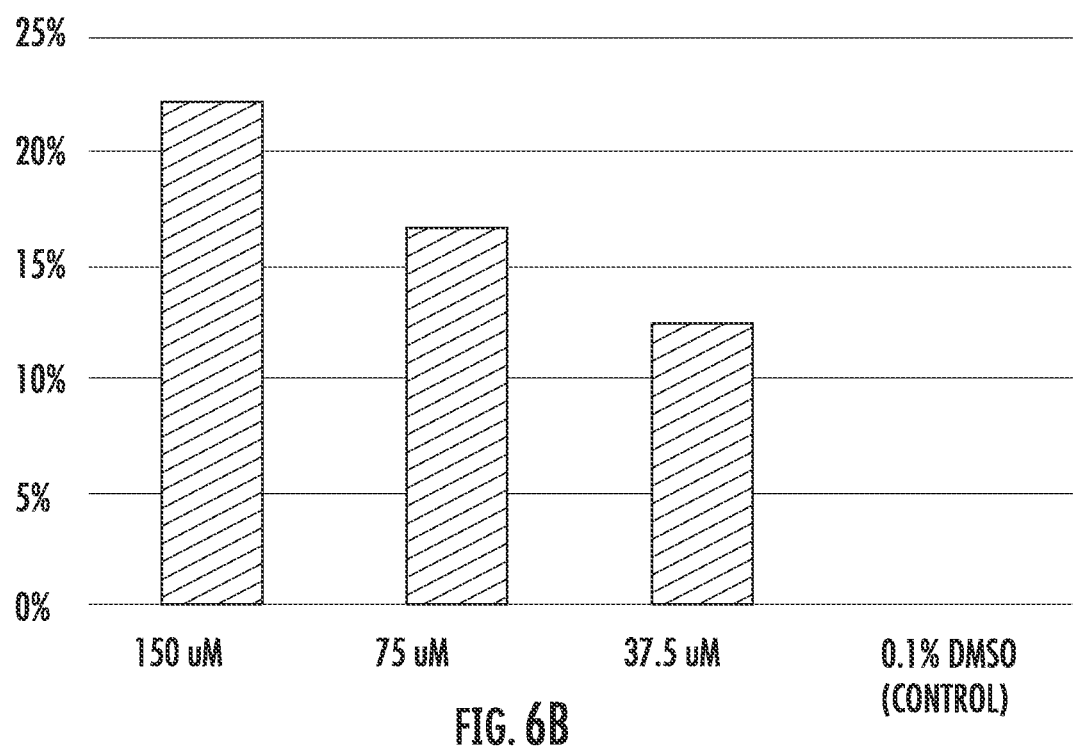
Figure 7A:
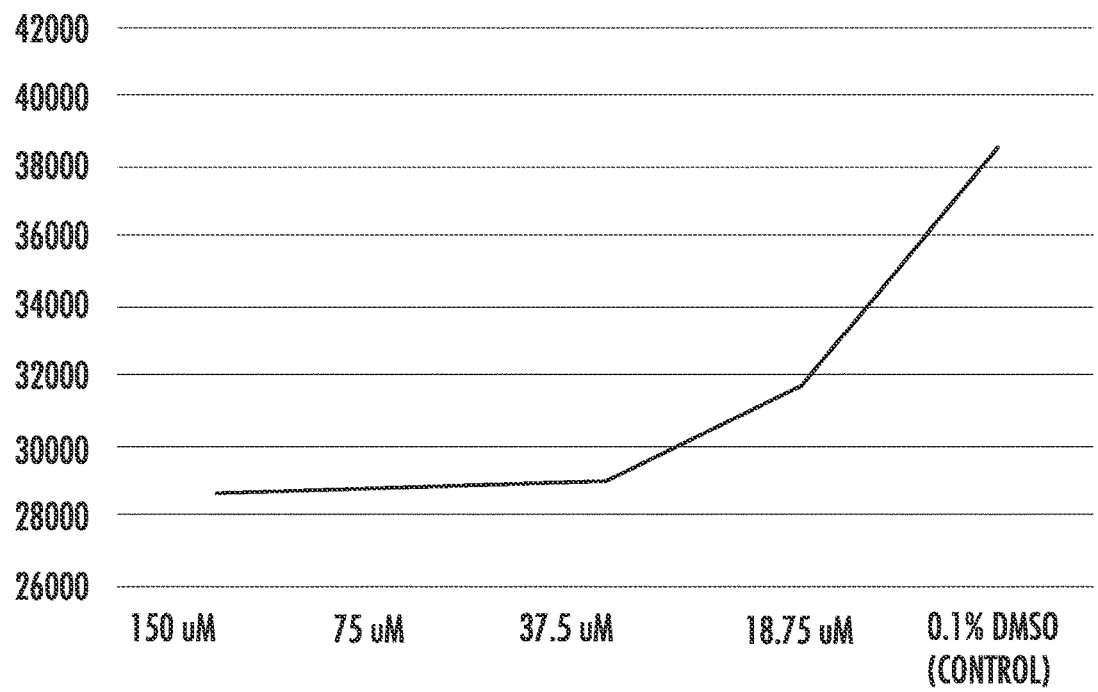
FIGS. 7(a) and 7(b) show compound a inhibits the growth of human h727 lung tumor cells.
Figure 7B:
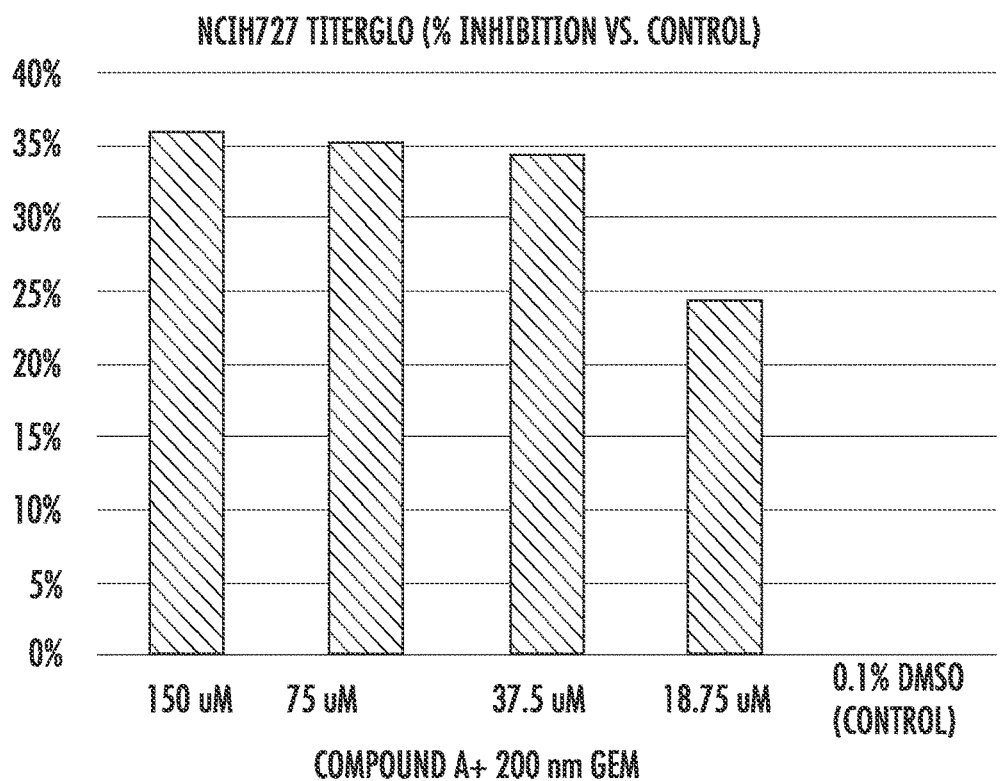
Figure 8A:
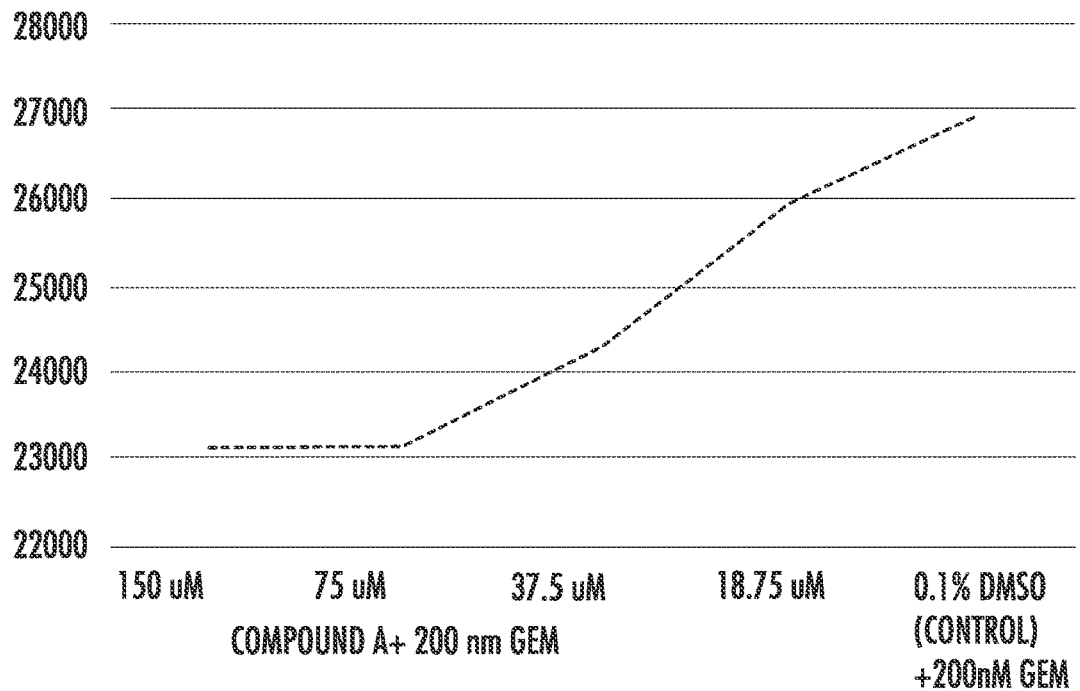
FIGS. 8(a) and 8(b) show compound a potentiates gemcitabine growth inhibition of human h727 lung tumor cells.
Figure 8B:
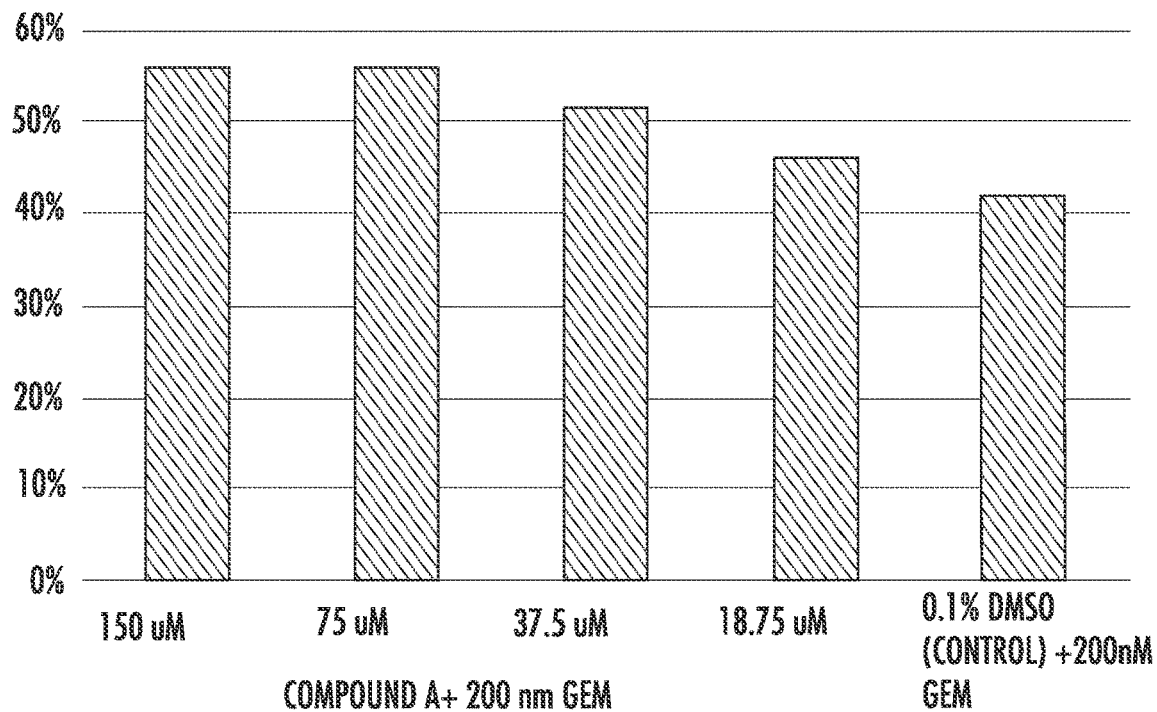

FIGS. 4(a) and 4(b) show Compound A inhibits the growth of human mkn1 gastric tumor cells. FIGS. 5(a) and 5(b) show Compound A synergistic impact on gemcitabine growth inhibition of human mkn1 gastric tumor cells. FIGS. 6(a) and 6(b) show COMPOUND A inhibits the growth of human hct116 colorectal tumor cells. FIGS. 7(a) and 7(b) show Compound A inhibits the growth of human h727 lung tumor cells. FIGS. 8(a) and 8(b) show Compound A potentiates gemcitabine growth inhibition of human h727 lung tumor cells.

The ability of COMPOUND A to inhibit the growth of the solid tumor cell lines shows promise for developing an anti cancer therapeutics that can selectively target GPR55/SCL15A1 co-expressing tumors. COMPOUND A may provided advantages over other GPR55 antagonists in that it is co-targeted to SLC15A1 on the cell surface. This co-targeting may also increase the bioavailability of COMPOUND A relative to other GPR55 antagonists in vivo.

Many modifications and other examples of the disclosure set forth herein will come to mind to those skilled in the art to which this disclosure pertains, having the benefit of the teachings presented in the foregoing descriptions and the associated drawings. Therefore, it is to be understood that the disclosure is not to be limited to the specific examples disclosed and that modifications and other embodiments are intended to be included within the scope of the appended claims.

Moreover, although the foregoing descriptions and the associated embodiments describe aspects of the disclosure in the context of certain example combinations of structural elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A compound represented by Formula I,

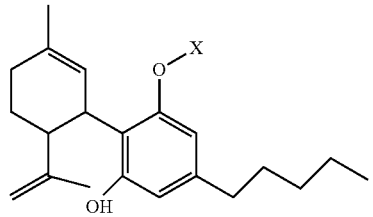

Formula I wherein:

X is

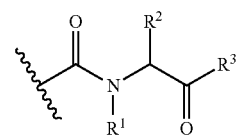

Formula X-a wherein:

$R^1$ is selected from the group consisting of H, $C_{1-10}$ alkyl, $C_{1-4}$ alkyl-aryl, $C_{1-4}$ alkyl-heteroaryl;

$R^2$ is H or $C_{1-10}$ alkyl optionally substituted with OH, SH, $SC_{1-4}$ alkyl, heteroaryl, CONH2, COOH, NH2, NHC(NH)NH2, or aryl, wherein the heteroaryl and aryl is optionally substituted with CN, halogen, $CF_3$, $C_{1-4}$ alkyl or OH;

and $R^3$ is selected from the group consisting of $C_{1-10}$ alkyl, $C_{1-4}$ alkyl-aryl, $C_{1-4}$ alkyl-heteroaryl, and

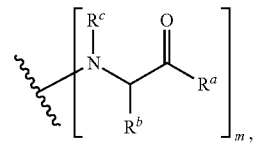

wherein
R$^a$ in each instance is OH, or OC$_{1-10}$alkyl, provided that R$^a$ is a covalent bond when R$^a$ is in a non-terminal position;
R$^b$ in each instance is independently H or C$_{1-10}$ alkyl optionally substituted with OH, SH, SC$_{1-4}$ alkyl, heteroaryl, CONH2, COOH, NH2, NHC(NH)NH2, or aryl, wherein the heteroaryl and aryl is optionally substituted with CN, halogen, CF$_3$, C$_{1-4}$ alkyl or OH;
R$^c$ in each instance is independently selected from the group consisting of H, C$_{1-10}$ alkyl, C$_{1-4}$ alkyl-aryl, C$_{1-4}$ alkyl-heteroaryl, wherein R$^b$ and R$^c$ optionally link up to form a 5 to 7 membered ring;
and m is an integer ranging from 1 to 9.

2. The compound of claim 1, wherein X is Formula X-a

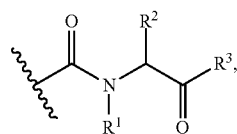

wherein R$^3$ is

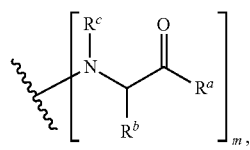

R$^1$ is H, R$^c$ is H, m is 1-4.

3. The compound of claim 2, wherein R$^2$ is C$_{1-4}$ alkyl optionally substituted with OH, SH, SMe, or NH2; R$^a$ is OH, R$^b$ is C$_{1-4}$ alkyl optionally substituted with OH, SH, SMe, CONH2, COOH, NH2, or NHC(NH)NH2; m is 1.

4. The compound of claim 1, having the structure

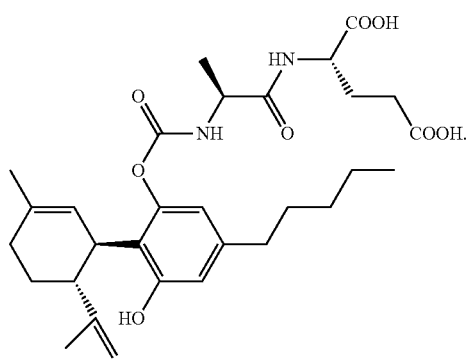 [SMILES: C=C(C)[C@@H]1CCC(C)=C[C@H]1c1c(O)cc(CCCCC)cc1OC(=O)N[C@@H](C)C(=O)N[C@@H](CCC(=O)O)C(=O)O]

5. The compound of claim 2, wherein each

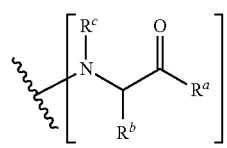

of R$^3$ is independently derived from lysine, leucine, isoleucine, glycine, aspartic acid, glutamic acid, methionine, alanine, valine, proline, histidine, tyrosine, serine, arginine, asparagine, glutamine, cysteine, threonine, phenylalanine and tryptophan.

6. The compound of claim 5, wherein R$^2$ is H or C$_{1-4}$ alkyl.

7. The compound of claim 6, wherein m is 1.

8. The compound of claim 7, wherein R$^2$ is H or methyl.

9. The compound of claim 7, wherein R$^b$ in each instance is independently H or C$_{1-10}$ alkyl optionally substituted with COOH.

10. A pharmaceutical composition comprising a therapeutically effective amount of a compound represented by Formula I,

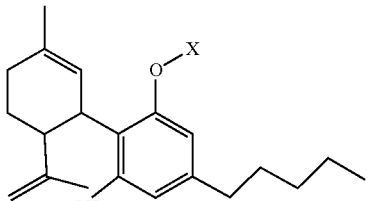

Formula I wherein:
X is

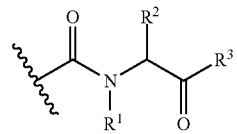

Formula X-a wherein:
R$^1$ is selected from the group consisting of H, C$_{1-10}$ alkyl, C$_{1-4}$ alkyl-aryl, C$_{1-4}$ alkyl-heteroaryl;
R$^2$ is H or C$_{1-10}$ alkyl optionally substituted with OH, SH, SC$_{1-4}$ alkyl, heteroaryl, CONH2, COOH, NH2, NHC(NH)NH2, or aryl, wherein the heteroaryl and aryl is optionally substituted with CN, halogen, CF$_3$, C$_{1-4}$ alkyl or OH;
and R$^3$ is

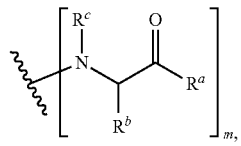

wherein
R$^a$ in each instance is OH, NHC$_{1-10}$alkyl or OC$_{1-10}$alkyl, provided that R$^a$ is a covalent bond when R$^a$ is in a non-terminal position;
R$^b$ in each instance is independently H or C$_{1-10}$ alkyl optionally substituted with OH, SH, SC$_{1-4}$ alkyl, heteroaryl, CONH2, COOH, NH2, NHC(NH)NH2, or aryl, wherein the heteroaryl and aryl is optionally substituted with CN, halogen, CF$_3$, C$_{1-4}$ alkyl or OH;
R$^c$ in each instance is independently selected from the group consisting of H, C$_{1-10}$ alkyl, C$_{1-4}$ alkyl-aryl, C$_{1-4}$ alkyl-heteroaryl, wherein $R^b$ and $R^c$ optionally link up to form a 5 to 7 membered ring;

and m is an integer ranging from 1 to 9.

11. The pharmaceutical composition of claim 10, wherein each

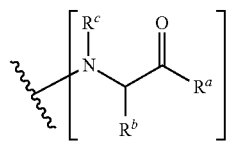

of $R^3$ is independently derived from lysine, leucine, isoleucine, glycine, aspartic acid, glutamic acid, methionine, alanine, valine, proline, histidine, tyrosine, serine, arginine, asparagine, glutamine, cysteine, threonine, phenylalanine and tryptophan.

12. The pharmaceutical composition of claim 11, wherein $R^1$ and $R^2$ are each independently selected from the group consisting of H, $C_{1-10}$ alkyl, $C_{1-4}$ alkyl-aryl, and $C_{1-4}$ alkyl-heteroaryl.

13. The pharmaceutical composition of claim 10, wherein the compound has the structure

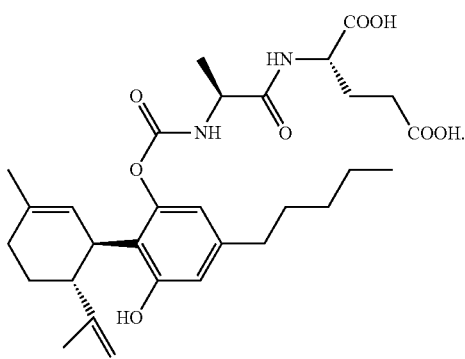 [SMILES: C=C(C)[C@@H]1CCC(C)=C[C@H]1c1c(O)cc(CCCCC)cc1OC(=O)N[C@@H](C)C(=O)N[C@@H](CCC(=O)O)C(=O)O]

14. A pharmaceutical composition comprising a therapeutically effective amount of the compound of claim 1.

15. The pharmaceutical composition of claim 12, wherein $R^1$ is H, $R^c$ is H, and $R^2$ is H or $C_{1-4}$ alkyl, m is 1 to 4.

16. The pharmaceutical composition of claim 15, wherein m is 1.

17. The pharmaceutical composition of claim 16, wherein $R^2$ is methyl.

18. The pharmaceutical composition of claim 15, wherein $R^b$ in each instance is independently H or $C_{1-4}$alkyl optionally substituted with COOH.

19. A kit comprising the compound of claim 1 and a secondary agent selected from the group consisting of an antimetabolite, a mitotic inhibitor, an alkylating agent, a platinum-based antineoplastic, an antibody based EGFR inhibitor, an antibody based HER2/3 inhibitor, an angiogenesis inhibitor, a mTOR inhibitor, a CDK4 and CDK6 inhibitor or an aromatase inhibitor.

20. The kit of claim 19, wherein the secondary agent is gemcitabine.

21. A method of treating a disease in a subject comprising administering to the subject a therapeutically effective amount of the compound of claim 1, wherein the disease is selected from the group consisting of lung cancer, gastric cancer, prostate cancer, pancreatic ductal adenocarcinoma, and colorectal cancer.

22. The method of claim 21, wherein the disease is selected from the group consisting of lung cancer, gastric cancer, and prostate cancer.

23. The method of claim 21, wherein the disease is pancreatic ductal adenocarcinoma or colorectal cancer.

24. The method of claim 21, wherein the disease is pancreatic ductal adenocarcinoma.

25. The method of claim 21, wherein the disease is colorectal cancer.

26. The method of claim 21, wherein the disease is lung cancer.

27. The method of claim 21, wherein the disease is gastric cancer.

* * * * *